(12) United States Patent
Yang et al.

(10) Patent No.: US 7,242,833 B2
(45) Date of Patent: Jul. 10, 2007

(54) METHOD AND APPARATUS FOR HIGH RESOLUTION COHERENT OPTICAL IMAGING

(75) Inventors: Victor Xiao Dong Yang, Toronto (CA); I. Alex Vitkin, Toronto (CA); Louis M. WongKeeSong, Rochester, MN (US); Sharon Katz, Windsor (CA); Margaret Leslie Gordon, Toronto (CA); Brian C. Wilson, Toronto (CA); Alvin Ho Kwan Mok, Richmond Hill (CA)

(73) Assignee: University Health Network, Toronto, Ontario (CA)

( * ) Notice: Subject to any disclaimer, the term of this patent is extended or adjusted under 35 U.S.C. 154(b) by 193 days.

(21) Appl. No.: 10/311,358

(22) PCT Filed: Jul. 10, 2001

(86) PCT No.: PCT/CA01/00992

§ 371 (c)(1),
(2), (4) Date: Nov. 13, 2003

(87) PCT Pub. No.: WO02/04929

PCT Pub. Date: Jan. 17, 2002

(65) Prior Publication Data

US 2004/0076390 A1 Apr. 22, 2004

Related U.S. Application Data

(60) Provisional application No. 60/217,090.

(51) Int. Cl.
  *G02B 6/04* (2006.01)
  *A61B 1/07* (2006.01)
(52) U.S. Cl. .................. 385/117; 385/115; 385/116; 600/182
(58) Field of Classification Search ......... 385/115–119
   See application file for complete search history.

(56) References Cited

U.S. PATENT DOCUMENTS

| 5,321,501 | A | 6/1994 | Swanson et al. |
| 5,459,570 | A | 10/1995 | Swanson et al. |
| 6,175,669 | B1 | 1/2001 | Colston et al. |
| 6,419,484 | B1 | 7/2002 | DaSilva et al. |
| 6,640,014 | B1 * | 10/2003 | Price et al. .............. 382/255 |

FOREIGN PATENT DOCUMENTS

| EP | 0 470 942 | * | 2/1992 |
| EP | EP 0 470 942 A1 | | 12/1992 |
| WO | WO 99/57507 | | 11/1999 |

OTHER PUBLICATIONS

Boppart, S.A., Bouma, B.E., Pitris, C., Southern, J.F., Brezinski, M.E., and Fujimoto, J.G. "In vivo Cellular Optical Coherence Tomography Imaging", Nature Medicine, vol. 4, No. 7, 861-865, Jul. 1998.

(Continued)

*Primary Examiner*—Michelle Connelly-Cushwa
(74) *Attorney, Agent, or Firm*—Peter A. Borsari

(57) ABSTRACT

A method and an apparatus for examining the subsurface microstructure of a sample are provided. Radiation from a plurality of optical radiation sources travels along a first optical path. In the first optical path, a device focuses the optical radiati n from each of the optical sources into a plurality of respective focal points along the first optical path to provide substantially continuous coverage of a selected portion of the first optical path. Then, a sample on the first optical path within the selected length extending into the sample is scanned along said selected portion of the first optical path.

27 Claims, 24 Drawing Sheets

OTHER PUBLICATIONS

Rollins, A.M., Kulkarni, M.D., Yazdanfar, S., Ung-Arunyawee, R., and Izatt, J.A. "In vivo Video Rate Optical Coherence Tomography", Optics Express, vol. 3, No. 6: 219-229, Sep. 14, 1998.

Schmitt, J.M., Lee, S.L., and Yung K.M. "An Optical Coherence Microscope with Enhanced Resolving Power in Thick Tissue", Optics Communications, 142: 203-207, 1997.

Schmitz, C.H., Graber, H.L., Barbour, R.L., "A fast versatile instrument for dynamic optical tomography", Optical Society of America -1999, pp. 1-3.

Tearney, G.J., Bouma, B.E., and Fujimoto, J.G. "High-speed phase and group delay scanning with a grating based phase control line" Optics Letters, vol. 22, No. 23, p. 1811-1813.

Tearney, G.J., Brezinski, M.E., Bouma, B.E., Boppart, S.A., Pitris, C., Southern, J.F., and Fujimoto, J.G. "In vivo Endoscopic Optical Biopsy with Optical Coherence Tomography", Science, 276: 2037-2039, Jun. 27, 1997.

Page from website http://hft.e-technik.uni-dortmund.de/uk/forschng/pic_oct.1.html, printed on May 3, 2000 —Chair of High Frequency Technique—Research—optical OCT sensor.

Pages from website http://hft.e-technik.uni-dortmund.de/uk/forschng/octsensoruk.html, printed on May 3, 2000—Chair of High Frequency Technique—Research—Sensor for the Optical Coherence Tomography (OCT).

* cited by examiner

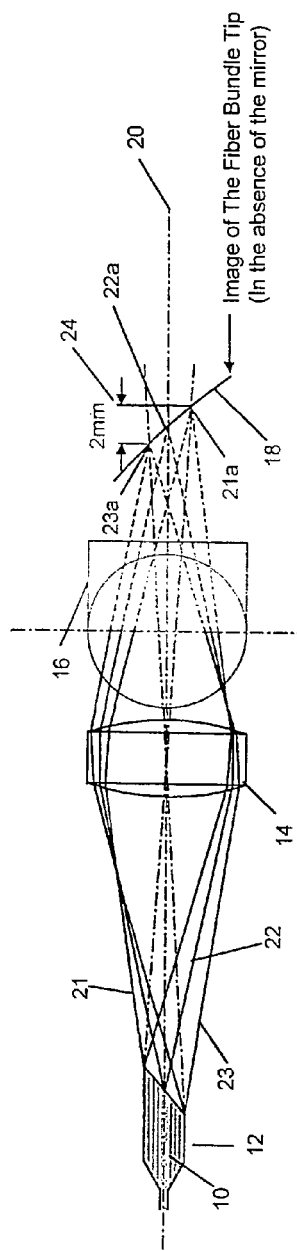
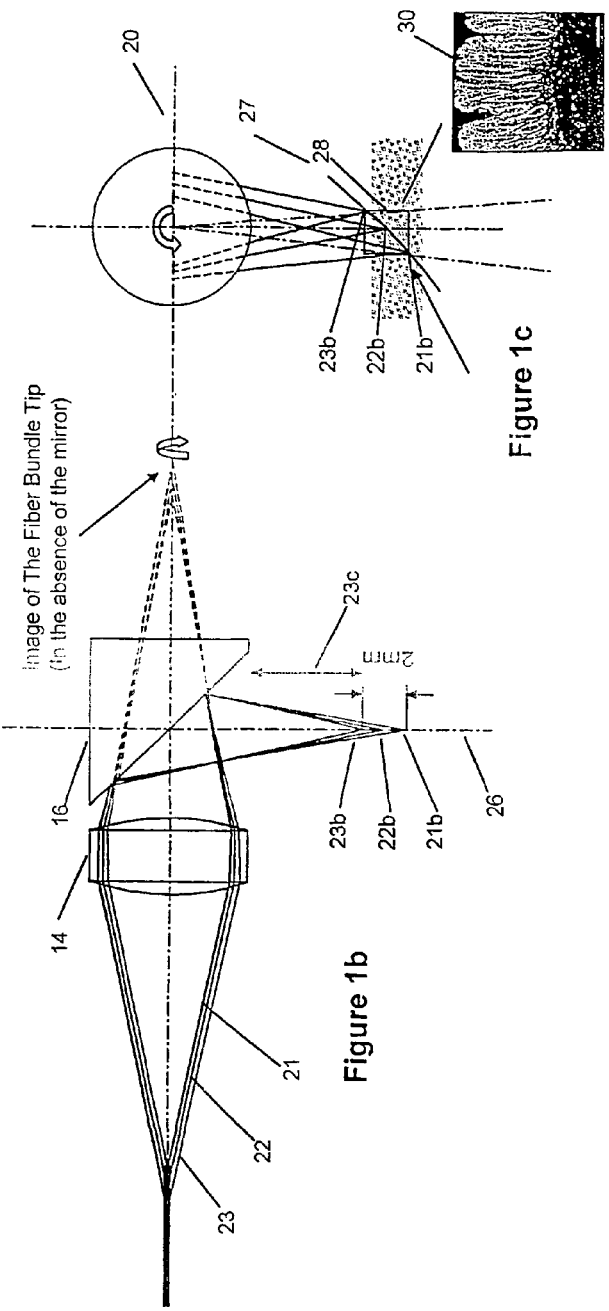
Figure 1a
Figure 1b
Figure 1c

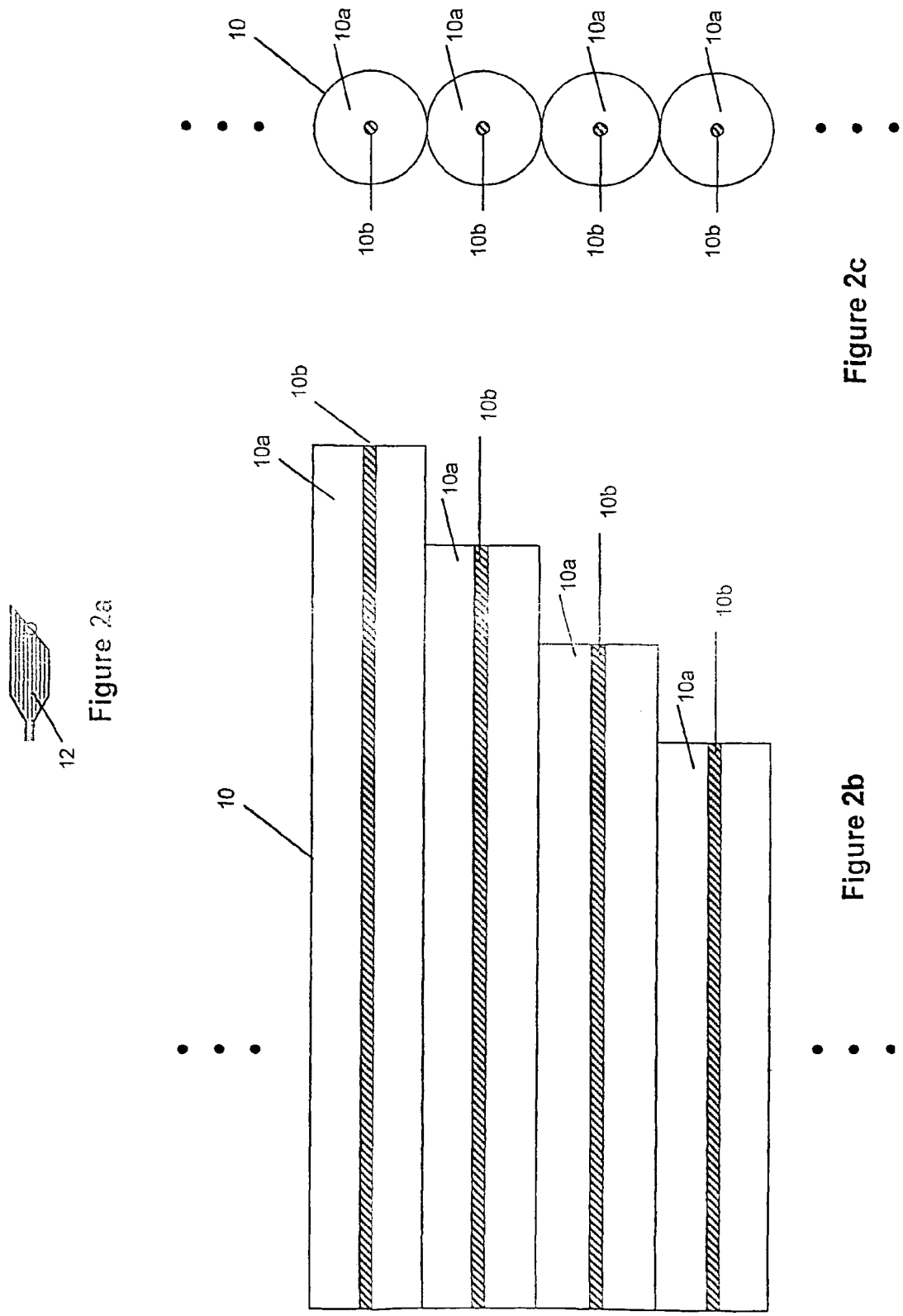

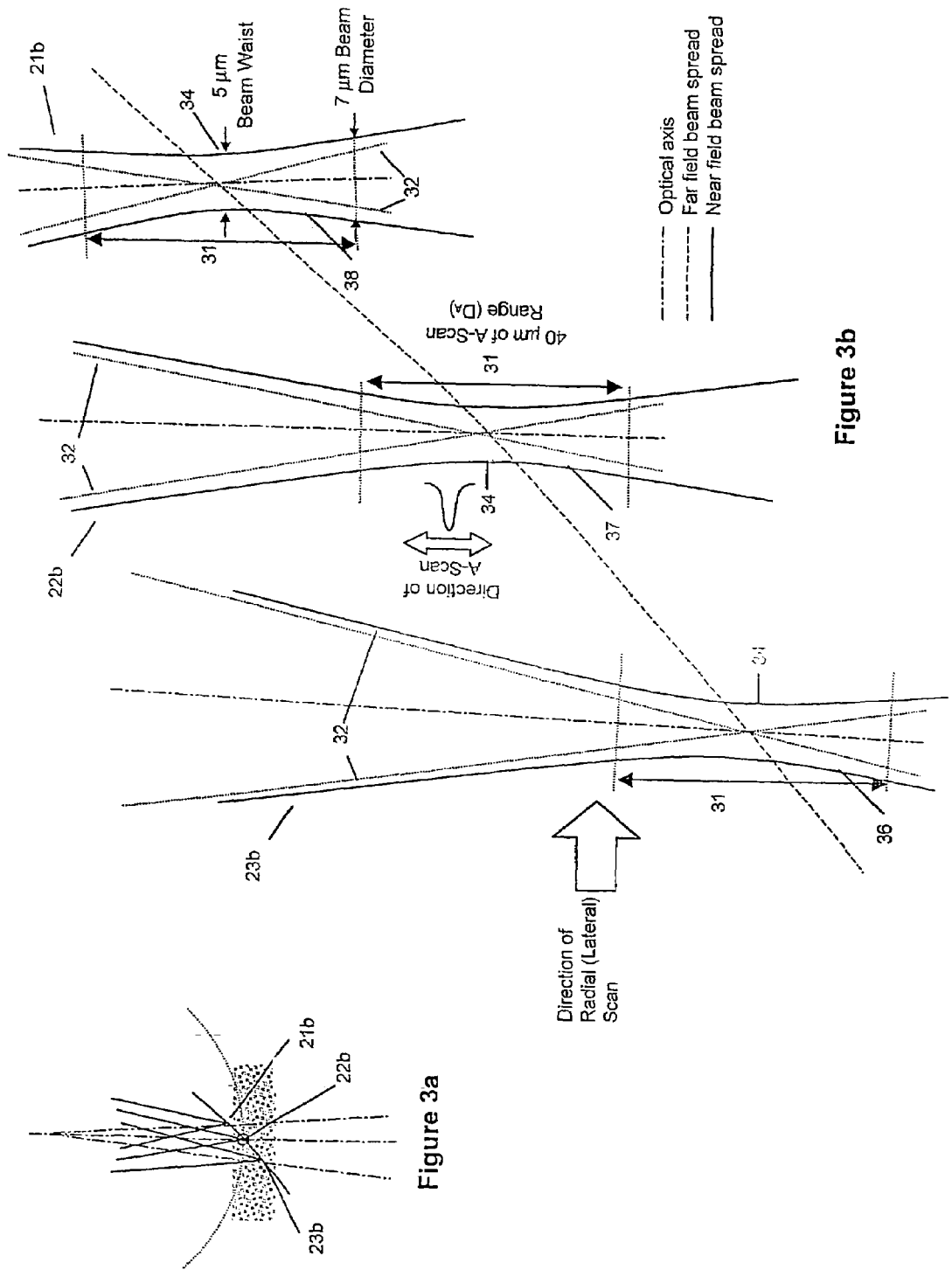

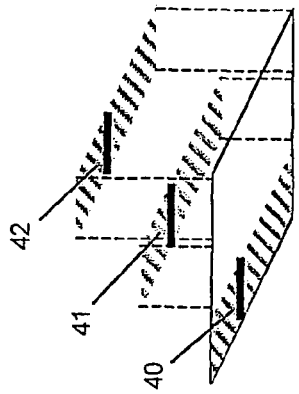
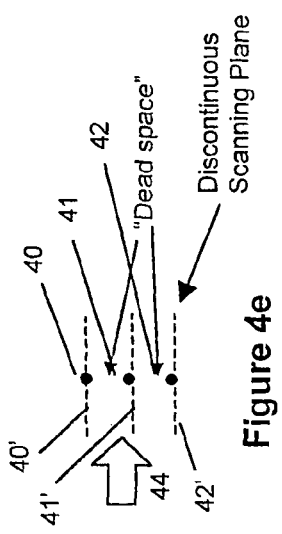
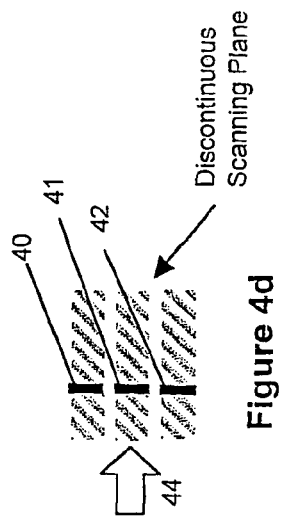
Figure 4f
Figure 4e
Figure 4d
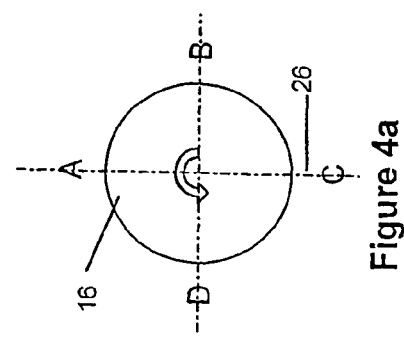
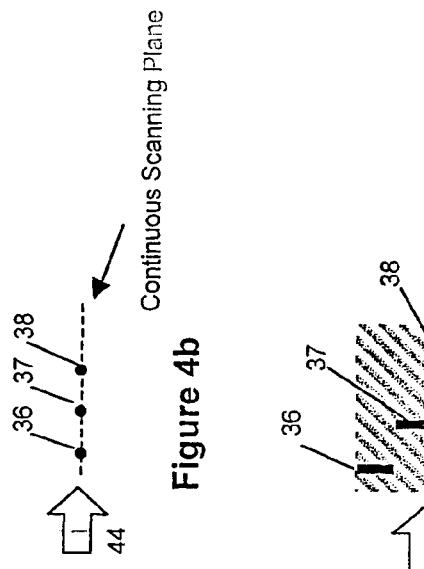
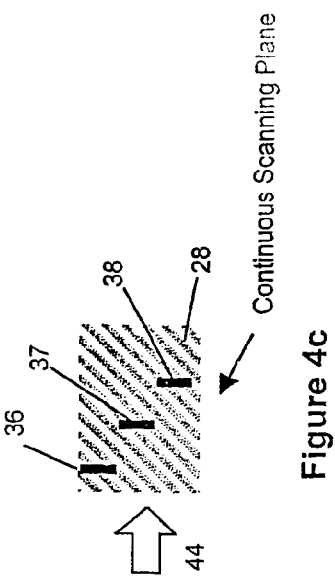
Figure 4a
Figure 4b
Figure 4c

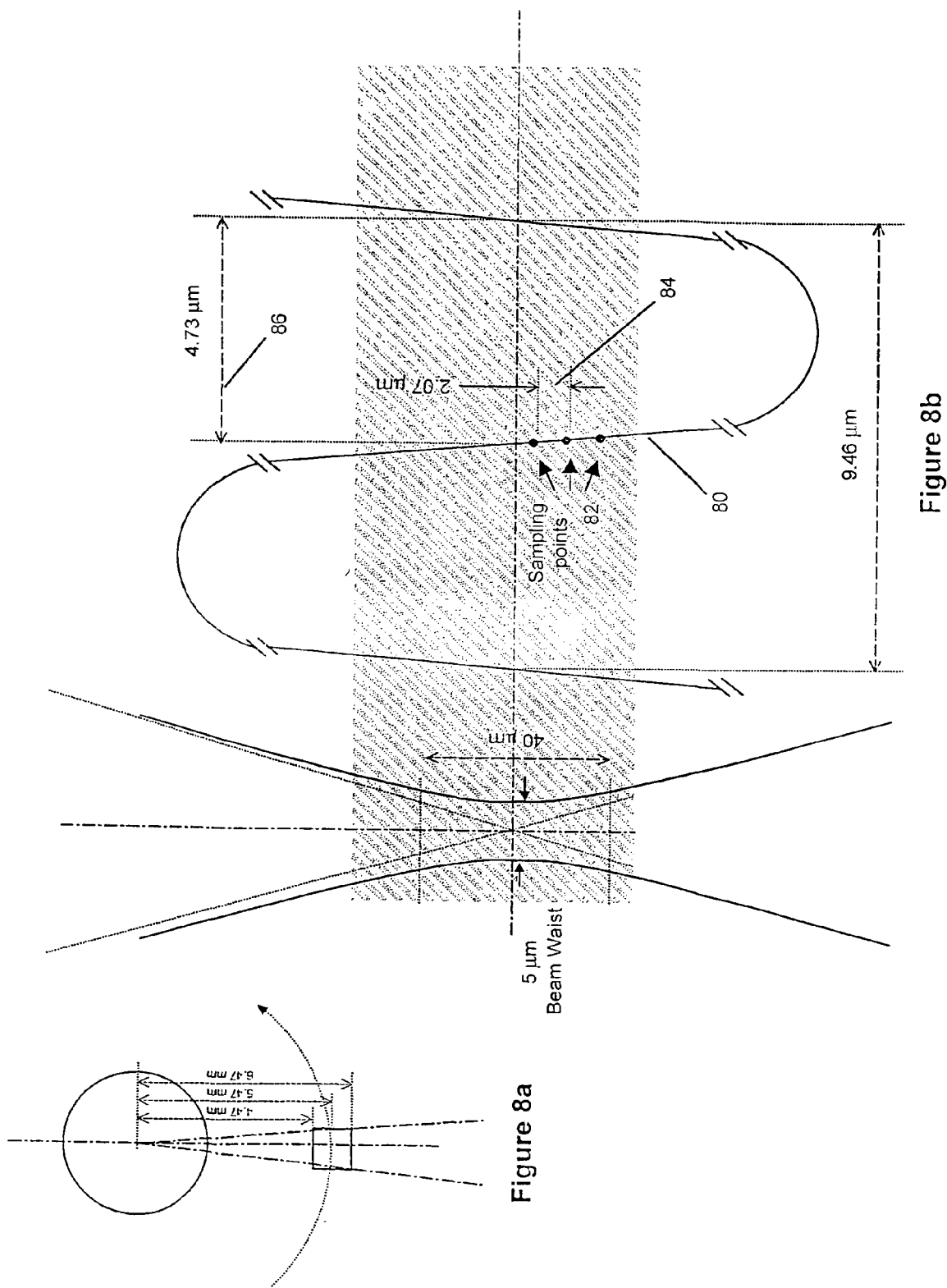

"Prior Art"

METHOD AND APPARATUS FOR HIGH RESOLUTION COHERENT OPTICAL IMAGING

FIELD OF THE INVENTION

This invention relates to both a method and an apparatus for high-resolution optical imaging. More particularly, this invention is concerned with providing high-resolution imaging suitable for incorporation into an endoscope.

BACKGROUND OF THE INVENTION

Modern medical imaging techniques have important applications in health care. Modalities such as X-ray computed tomography (CT), magnetic resonance imaging (MRI) and ultrasound imaging are the main tomographic techniques available in most modern medical centers. Visible-light endoscopy is another major imaging modality which is used extensively in procedures like bronchoscopy or colonoscopy. Each of these techniques employs different physical principles and measures different properties of the biological tissue under study With different resolution. Further, they can commonly be performed in-vivo. A third type of imaging, optical microscopy, is still utilized widely in clinical medicine. However, optical microscopy is currently limited to detailed examination of excised or resected specimens and is not used in-vivo. In many circumstances, the superior contrast and resolution afforded by optical microscopy is such that physical biopsy followed by optical microscopic histology is considered the gold standard for diagnosis.

Combinations of these techniques, such as using a low-resolution tomographic modality along with high-resolution imaging, biopsies or interventional procedures are constantly being studied and evaluated. Evaluation of these techniques is based on technological feasibility, clinical benefit and cost.

Optical Coherence Tomography (OCT) is a relatively new imaging technique based on the low-coherence property of electromagnetic radiation that enables high-resolution depth profilometry in a turbid, highly scattering media such as biological tissue. Its use in biomedical imaging is currently being investigated in several research and industrial laboratories. The main advantage of OCT lies in its ability to localize the depth of reflection from a sub-surface site in tissue. This localization is essentially determined by the coherence properties of the light source used and can be as low as 2 to 20 μm for selected near-IR sources (e.g. lasers or amplified spontaneous emission devices). This gives a measure of the depth resolution attainable with OCT. Independently of the coherence characteristics, the lateral resolution is determined by the beam cross-section at the depth of imaging and by the lateral spacing of the acquired data. Typical values for lateral spacing in the literature are in the 5 to 30 μm range. The price to be paid for this remarkable cross-sectional imaging ability in intact turbid tissue is the limited imaging depth since, due to multiple scattering and absorption, both coherence and penetration of light are degraded resulting in OCT imaging depths of approximately 2 to 3 mm.

Most current implementations of OCT are based on Michelson interferometry with a 50/50 beam splitter directing the incident coherent light beam into a reference path containing a mirror (i.e. a reference arm) and a sample path containing the interrogated sample (i.e. a sample arm). Both free-space optic and fiber-optic implementations of this scheme are currently used. Reflected beams from the mirror in the reference arm and from the tissue in the sample arm are recombined in the same splitter and half of the resultant light energy impinges on a detector. Incoherent superposition of the two light fluxes typically occurs except when the optical path lengths of the two beams are matched to within the coherence length of the source. Within this limited distance, the coherent superposition of the two light fluxes yields an interference pattern with a fringe magnitude that is proportional to the reflectivity of the tissue at that particular depth. Depth profiling of the sample is then achieved by scanning the reference arm length or more correctly by scanning the optical path length of the reference arm by using a time delay in the reference arm (this is equivalent to lengthening the reference arm). Various detection methods to measures and quantify these faint amplitude modulations amidst large background diffuse reflectance have been developed having a dynamic range of approximately 70 to 110 dB. Furthermore, lateral translation of the beam and axial motion of the reference mirror enables one to construct a two-dimensional reflectivity picture over a desired field of view. Means of improving the final image quality, such as performing image processing through de-convolution, have also been investigated.

The foregoing is a brief description of conventional reflectivity OCT imaging. Other variations include, for example, flow (Doppler) imaging and polarization imaging (albeit at the expense of additional, complexity of the OCT optics and/or signal processing techniques). Images from these additional techniques are usually obtained in conjunction with images from conventional OCT so some image overlay or fusion is possible. Upon further technological development and/or clinical implementation, may add sufficient information content to increase the clinical utility of OCT in medicine.

However, many OCT designs and approaches that have been successfully implemented in tabletop research systems are not directly suitable for in-vivo imaging such as in gastroenterologic or bronchoscopic endoscopy. Instead, they may be more suitable for dermatological, ophthalmologic and dental applications. In contrast, in-vivo OCT imaging must address the issues of speed, resolution, contrast, penetration and instrument size. Images must be obtained sufficiently quickly to negate the effects of patient motion while still achieving suitable axial and lateral resolution; and maintaining an instrument size which is small enough to be endoscopically useful. Powerful near-IR sources, fast means of altering the reference arm length and custom-designed distal optical devices have been successfully developed to overcome the difficult challenges posed by in-vivo endoscopy.

The latest OCT technology employs a single-mode optical fiber with distal side-viewing optics introduced into the accessory channel of a conventional white-light endoscope. To build-up an image, the viewing direction of the OCT fiber is either linearly scanned to and fro over an approximate 2 mm distance, or is rotated via a flexible guide-wire or interlocking gear mechanism at several revolutions per second. Simultaneous with this translation or rotation, the reference arm length outside the endoscope is rapidly varied via an optical phase delay to generate depth scans (i.e. A-scans). Currently, these OCT systems operate at frame rates up to conventional video rates but more typically at 4 to 8 frames per second, with a frame presenting a fully circumferential view to a depth of 2 to 3 mm. The resultant resolution values are approximately 5 to 25 μm in the depth (axial) direction and approximately 20 to 40 μm in the lateral direction. As well, the lateral resolution generally degrades with an increase in distance from the fiber tip of the OCT device due to geometric divergence. These OCT systems have a dynamic range which is somewhat lower than that of corresponding ex-vivo systems due to increased noise levels and faster imaging speeds.

Based on the latest OCT technology, it is questionable whether coherent in-vivo OCT systems are adequate for successful clinical imaging. The images are certainly useful, but substantial improvement is required if the elusive goal of "optical biopsy" is to be realized. For example axial and lateral resolution can be improved. While the improvement in the former usually involves the use of better low-coherence sources (i.e. CW and pulsed sources), the issue of sub-optimal and depth-varying lateral resolution is more difficult to address. In ex-vivo systems, with its relaxed constraints of speed and physical size, lateral resolution is improved by focusing the beam to a few microns with a high-NA (numerical aperture) objective lens. In contrast to conventional OCT scanning, the imaging can now be performed in the lateral (en face) direction with a pre-selected depth with small oscillations in path length difference, followed by a small depth increment as necessary. The high-NA objective lens is often coupled to tissue via a refractive-index matching liquid. The general approach of using OCT with a high-NA distal optic lens is known as Optical Coherence Microscopy (OCM). However, the improved lateral resolution at the beam waist location comes at the expense of lateral blurring at other depths because the highly focused beam has a very shallow depth of field. Thus, the lens-to-surface distance must be varied to focus to different depths. In addition, a dynamic tracking scheme is needed to keep the location of the coherence gate (within which coherent interference between the optical beams from the sample arm and the reference arm is possible) and the beam waist at the same depth. These techniques for lateral resolution improvement have not been attempted during in-vivo endoscopy because of size and speed requirements.

SUMMARY OF THE INVENTION

The present invention is based on the concept of providing an endoscopic optical coherence tomography (OCT) device with microscopic resolution which will hereinafter be referred to as an endomicroscope. After reviewing possible clinical applications of the endomicroscope, the following parameters and features were identified since it is difficult to achieve these parameters and features simultaneously with current in-vivo OCT systems.

1. High Resolution

In order to achieve cellular and sub-cellular resolution, an endomicroscope should preferably resolve features smaller than 5 µm both in the axial and lateral directions. In contrast to most existing in vivo OCT systems, the lateral resolution must not degrade substantially with the depth of the tissue being imaged due to geometric divergence.

2. Large Field of View

An appropriate field of view of the endomicroscope is approximately 2×2 mm in the axial and lateral directions of the optical axis This field of view is considered to be adequate for clinical applications. In order to achieve a 5 µm resolution in both the axial and lateral directions throughout the entire image, more than 800 A-scans (i.e. depth scans) have to be performed for each frame. The resultant image will contain more than 640,000 pixels. This is several orders of magnitude higher than existing in vivo OCT systems.

3. Small Size of Endoscope Tip

Most of the existing in vivo OCT systems are designed around the constraints of the instrument channel of existing endoscopes. As a result, the outer diameter of these systems is restricted to approximately 2 to 3 mm which limits the numerical aperture of the imaging system. This makes it difficult to obtain high lateral resolution under in vivo conditions. These constraints may be technically unnecessary and limit one from fully exploiting the benefit of OCT/OCM in the clinical applications under consideration. Accordingly, a larger outer diameter, such as 3 mm or more, for example, may be used for the endoscope as well as a length of less than 20 mm for the rigid tip.

4. High Imaging Speed

Since the endomicroscope will be used to image a large area at high resolution under in vivo conditions, motion artifacts must be considered because of tissue motion due to physiological motion. These motion artifacts should be eliminated to ensure good image quality. Accordingly, the endomicroscope should preferably be able to acquire a single frame image within 12.6 ms given a typical physiological motion speed of 5 mm/s. This results in 63,000 A-scans per second. This imaging speed is more than one order of magnitude higher than that of current in vivo OCT systems.

5. Integration with Currently Available Endoscopic Imaging Procedures

In order to improve clinical usefulness, conventional white light imaging should preferably be integrated into the endomicroscope. In addition, instrument channels should be preferably designed so that an excisional biopsy could be performed under the guidance of the endomicroscope. As well, instrument channels for water and air delivery may be preferably made available.

The advanced requirements for an endomicroscope outlined above are not compatible with existing OCT/OCM designs. For instance, if an outer diameter of 6 mm is allowed for the endomicroscope and a distal optical design is used based on a single rotating fiber as described by Tearney, G. J., Brezinski, M. E., Bouma, B. E., Boppart, S. A., Pitris, C., Southern, J. F., and Fujimoto, J. G. ("In vivo Endoscopic Optical Biopsy with Optical Coherence Tomography", Science, 276: 2037–2039, Jun. 27, 1997), then although the 5 µm lateral resolution can be achieved at a single specific depth within the tissue in any one scan, such lateral resolution will degrade due to beam divergence at other depths. In addition, since a high NA system will be required to produce the requisite small beam waist size, the coherence gate and the focal point will not stay together in depth over a substantial (e.g. 2 mm) distance unless some dynamic compensation is implemented as described by Schmitt, J. M., Lee, S. L., and Yung, K. M ("An Optical Coherence Microscope with Enhanced Resolving Power in Thick Tissue", Optics Communications, 142: 203–207, 1997). Therefore, in order to achieve some of the aforementioned requirements of the endomicroscope, dynamic focusing (changing the probe/tissue distance) and dynamic compensation (charging the path length difference) must be used. However, these focusing and compensation techniques complicate the practical realization of the device and may make it more difficult to satisfy the high imaging speed requirement. If one tries to first satisfy the imaging speed, as described by Rollins, A. M., Kulkarni, M. D., Yazdanfar, S., Ung-arunyawee, R., and Izatt, J. A. ("In vivo Video Rate Optical Coherence Tomography", Optics Express, Vol. 3 No. 6: 219–229, 14 Sep. 1998), then image resolution, particularly lateral resolution, is degraded to an extent that the clinical utility of the device is compromised.

The present invention provides an endomicroscope with multiple fibers (i.e. channels) employing OCT to allow for different parts of the image to be scanned in parallel, instead of in series as is currently implemented in existing in vivo or ex vivo OCT/OCM systems. Using multiple parallel channels focused to different depths in the tissue, with each channel collecting high-resolution OCT data only across a very small axial range allows for a series of tight focal points to be achieved throughout the entire field of view without dynamic focusing or dynamic compensation. This greatly simplifies the design of the device which may now use mostly fixed optical components, and may facilitate high-speed operation. In addition, the intrinsically miniature dimension of the fiber optic based OCT technique makes the multichannel concept possible to implement in a flexible endoscopic device while the proximal part of the endoscope, which is outside of the patient, allows room for sources, detectors, and other equipment.

In accordance with a first aspect of the present invention, there is an apparatus for optical examination of a sample, the apparatus comprising:

an optical source means for providing a plurality of separate optical radiation sources;

a first optical path extending from the source means; and, a focusing means in the first optical path for focusing optical radiation from the optical radiation sources into a plurality of respective focal points located on a surface within the first optical path to provide substantially continuous coverage of a selected portion of the first optical path, whereby, in use, a sample can be located at least partially within the selected portion, thereby permitting simultaneous scanning of a plurality of points within the sample.

In accordance with a second aspect of the present invention, an N channel apparatus for optical examination of a sample, wherein the N channel apparatus comprises a plurality of optical networks and a reference arm, each optical network providing one channel for the N channel apparatus and sharing the reference arm.

In accordance with another aspect of the present invention, there is provided a method for optical examination of a sample, the method comprising:

(a) providing radiation from a plurality of separate optical radiation sources, along a first optical path;

(b) providing focusing means in the first optical path;

(c) focusing the optical radiation from the optical sources into a plurality of respective focal points along a surface within the first optical path to provide substantially continuous coverage of a selected portion of the first optical path; and (d) providing a sample located at least partially within the first optical path; and, (e) simultaneously scanning a plurality of points within the sample.

It is to be appreciated that a sample, for use with the present invention, may comprise any biological tissue or other suitable material.

Further objects and advantages of the invention will appear from the following description, taken together with the accompanying drawings.

BRIEF DESCRIPTION OF THE DRAWINGS

For a better understanding of the present invention and to demonstrate how it may be carried into effect, reference will now be made, by way of example, to the accompanying drawings which show a preferred embodiment of the present invention and in which:

FIG. 1a is a top view of tip of an apparatus in accordance with the present invention showing optical paths and ignoring the refraction effects of an air-tissue interface;

FIG. 1b is a side view of the tip of an apparatus in accordance with the present invention showing optical paths and ignoring the refraction effects of an air-tissue interface;

FIG. 1c is an end view of the tip of an apparatus in accordance with the present invention showing optical paths and ignoring the refraction effects of an air-tissue interface;

FIG. 2a shows the fiber bundle tip of FIG. 1;

FIG. 2b is a top view of an enlarged section of the fiber bundle tip;

FIG. 2c is an end view of an enlarged section of the fiber bundle tip;

FIG. 3a illustrates the focal points of three of the imaging fibers of the fiber bundle tip of FIG. 1;

FIG. 3b is a magnified view of the focal points of FIG. 3a showing details of the focal points at different depths;

FIG. 4a is a schematic indicating different directions for directing the optical beams from the fiber bundle tip of FIG. 1;

FIGS. 4b and 4c are top and end views of optical beams in directions A and C of FIG. 4a;

FIGS. 4d and 4e are top and side views of optical beams directed in directions B and D of FIG. 4a;

FIG. 4f shows a perspective view of the optical beams in the directions B and D;

FIG. 5c is a graph of beam spot diameter versus focal zone distance for the fiber bundle tip of FIG. 5a;

FIG. 7b is a front view of a scanning mirror used in the optical delay generator of FIG. 7a.

FIG. 8a is an end view of the mirror and the focal points from three of the imaging fibers of the fiber bundle tip of FIG. 1a;

FIG. 8b shows a combined A-scan and a two-dimensional brightness-mode (B-mode) scan path for light radiated from a single imaging fiber of the present invention;

FIG. 13b is an experimental result from experimentation on the setup of FIG. 13a;

FIG. 13c is another experimental result from experimentation on the setup of FIG. 13a;

DETAILED DESCRIPTION OF THE INVENTION

Figure 1D:
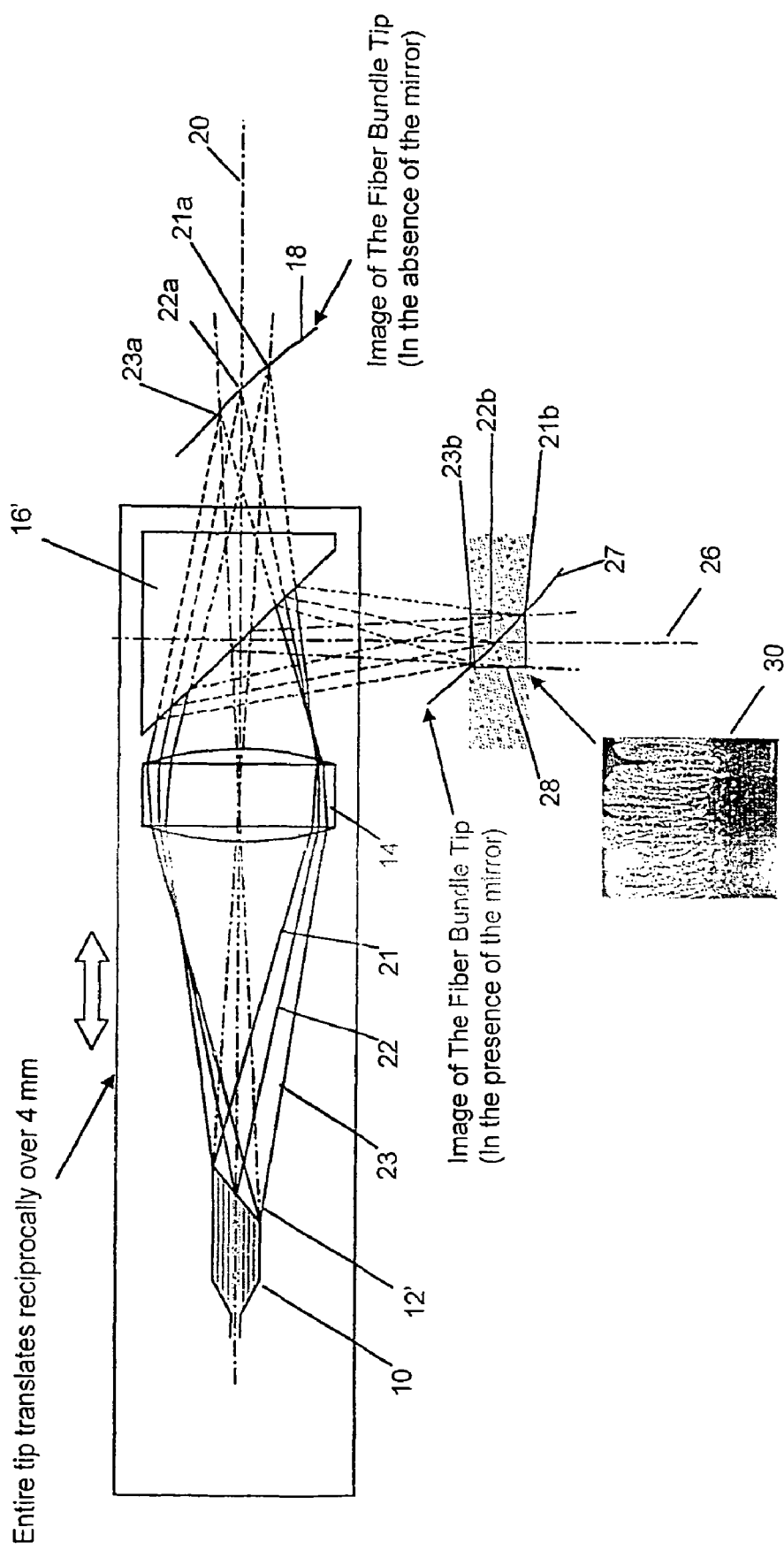
FIG. 1d is an alternate embodiment of the tip of the apparatus of FIG. 1a showing optical paths and ignoring the refraction effects of an air-tissue interface.

In the following description, various specific dimensions and other parameters are mentioned such as the wavelength used by the imaging source and the physical dimensions of the optical components used in the apparatus. It is to be appreciated that this is for exemplary purposes only and does not limit this invention. Specific parameters, dimensions and the like may be chosen depending on an intended application of the invention.

Referring to FIG. 1, the present invention provides an apparatus comprising an endoscopic coherent optical microscope having multiple single mode fibers 10, a fiber bundle tip 12, a focusing lens 14 and a mirror 16. The multiple single mode fibers 10 and the focusing lens 14 are stationary while the mirror 16 is rotatable. Accordingly, the mirror 16 is mounted for rotation in known manner. Details of the rotating mechanism for the mirror 16 are not described further and can be conventional. Multiple single mode fibers 10 (of which there may be approximately 50 fibers) form an array at the fiber bundle tip 12. This array is cleaved and arranged in a "staircase" pattern as shown in FIG. 2. Radiated light from the fiber bundle tip 12 is focused by the focusing lens 14 and reflected by the mirror 16. The focusing lens 14 may have a diameter of 5 mm (i.e. ϕ=5 mm) and a focal length of 5 mm (i.e. f=5 mm). The mirror 16 may have a diameter of 5 mm and a front face that is cleaved at 45°. A magnified image of the focal points of the fiber bundle tip 12 is shown in FIG. 3.

FIG. 1a shows three beams 21, 22 and 23 from three exemplary fibers arbitrarily chosen from the multiple single mode fibers 10. Due to the staggered or staircase nature of the multiple single mode fibers 10 (see FIG. 2), each of the beams 21, 22 and 23 originates from a different point and consequently is brought into focus, by the focusing lens 14, at a different point 21a, 22a and 23a on a surface 18 when the mirror 16 is not used. It will be appreciated that a similar effect is achieved for all of the multiple single mode fibers 10 of the fiber bundle tip 12 to produce beams focused to different points on the surface 18. As indicated at 24 (and as shown in FIG. 3), if the multiple single mode fibers 10 comprise 50 optical fibers, each being focused within a short range of approximately 40 microns and having their ends staggered to space the focal points apart by 40 microns (as measured along axis 20 of the focusing lens 14), a total range or depth of 2 mm is covered. The axis 20 for the focusing lens 14 is part of a first optical path.

With the mirror 16 present, the optical beams 21, 22 and 23 are focused as shown in FIGS. 1b and 1c. Thus, three focal points 21b, 22b and 23b are spaced apart in a vertical or depth direction along axis 26 which forms an extension of the first optical path. As the view of FIG. 1c shows, the three focal points 21b, 22b and 23b are also spaced apart in the circumferential direction (i.e. they are spaced apart laterally) relative to the motion of the mirror 16. The three focal points 21b, 22b and 23b fall on a surface 27 to facilitate imaging of a selected portion of the first optical path. The surface 27 may be a complex surface or a planar surface. If multiple single mode fibers 10 comprises 50 individual fibers, then the focal points of all the individual fibers from the fiber bundle tip 12 would be spaced apart correspondingly. Alternatively, the reflected focal points 21b, 22b and 23b do not necessarily have to be perpendicular to the axis 20 but may be at a large angle to the axis 20.

Rotation of the mirror 16 results in motion of the surface 27. This enables a two-dimensional B-scan image 30 to be obtained, as shown in FIG. 1c, covering a scan area 28 which has a square shape with preferable dimensions of 2 mm×2 mm. The B-scan image 30 indicates an exemplary view that may be obtained for the scan area 28.

Redesigning the multiple single mode fibers 10, for example, by changing the diameter of the core and cladding of the multiple single mode fibers 10, results in variations on the surface 27. Furthermore, optical wave guide wafers may also be used in the place of the multiple single mode fibers 10.

In an alternative embodiment, the mirror 16 may be replaced by a mirror 16' that moves linearly in combination with the focusing lens 14 and the fiber bundle tip 12 as shown in FIG. 1d. The linear translation may preferably incorporate a reciprocal motion. In terms of mechanics, the fiber bundle tip 12, depicted in FIG. 1a, utilizes a radial scanning motion. The radial scanning motion is well suited for scanning organs having larger diameters, such as the esophagus or the large intestine. However, due to the complex driving mechanism needed for radial scanning, the diameter of the fiber bundle tip 12 will not allow for endomicroscopy in organs having small inner diameters such as blood vessels. Therefore, the alternative embodiment shown in FIG. 1d may be used which comprises a similar fiber bundle tip 12' that is adapted to perform linear translational scanning instead of radial scanning.

As shown in FIG. 1d, the main differences between the two methods of scanning are that the mirror 16' will not be rotating and the entire fiber bundle tip 12' needs to be translated along its horizontal axis in preferably a reciprocal motion over a range of 4 mm for example. Mechanically, the linear translational scanning motion is less complicated than the radial scanning motion. In addition, linear translational scanning is better suited for endomicroscopy in organs having a small inner diameter such as blood vessels. However, for some larger organs, such as the large intestine, linear translational scanning is not as well suited due to positioning difficulties.

In a further alternative embodiment, both of the scanning motions may be combined to produce an endomicroscopy device having helical scanning. The helical scanning motion would comprise the rotational movement of the mirror 16 in combination with the linear translation of the mirror 16, the focusing lens 14 and the fiber bundle tip 16. Such an endomicroscopy device may be more suitable for imaging certain types of organs such as the human large intestine. The helical scanning endomicroscopy device may be implemented by linearly translating the apparatus shown in FIG. 1a.

In yet another alternative embodiment, the fiber bundle tip 12 may be altered to employ a Micromachined Electro-Mechanical System (MEMS) driving mechanism. Since the aforementioned embodiments require some form of motion for the mirror 16, all embodiments require mechanical driving mechanisms. Accordingly, a motor is situated outside of the endoscope and a mechanical drive-train mechanism or wire is placed along the entire length of the endoscope. However, the multi-channel fiber optical design is not restricted to such mechanical driving means. In fact, due to the extremely small spatial resolutions realizable by the multi-channel system, adverse effects, such as vibration induced polarization dependence, from the mechanical drive means, may limit the full potential of the present invention if a mechanical drive means is utilized. Therefore, a MEMS electrical driving mechanism. may be employed where electrically-driven, micro-mechanical optical devices are used to facilitate the scanning. This implementation may potentially circumvent the adverse effects that may be caused by a mechanical driving mechanism since the MEMS implementation reduces vibrations along the axis of the device except in the vicinity of the object which is being translated such as the mirror 16. The MEMS implementation may also offer advantages in terms of miniaturization and performance.

In a further alternative embodiment, the fiber bundle tip may not require the mirror 16. The combination of the fiber bundle tip 12 and the focusing lens 14 may be pivotally attached. Accordingly, through a pivoting motion, the combination of the fiber bundle tip 12 and the focusing lens 14 may be adapted to direct a plurality of focusing points along portions of a plurality of surfaces extending into the sample to construct the B-scan image 30 of the scan area 28.

In yet another embodiment, the mirror 16 may be a surface of a prism. The rest of the apparatus would follow as previously described and shown in FIGS. 1a to 1d.

It should further be understood that the optical path can be straight, bent or curved. Furthermore, the optical path may be a 3 dimensional path having a length, width and height. Depending on the scanning motion (i.e. radial, linear or helical), the orientation of the surface, upon which the focal points reside, may also vary. Furthermore, the optical path may comprise optical radiation from one optical radiation source or a plurality of optical radiation sources (i.e. a plurality of light sources or a plurality of fibers each transmitting optical radiation).

Referring now to FIGS. 2b and 2c, a magnified view of the fiber bundle tip 12 comprising the multiple single mode fibers 10 is shown. Each of the multiple single mode fibers 10 comprises a cladding 10a around a core 10b having diameters of, for example, 40 µm and 5 µm respectively. The ends of the multiple single mode fibers 10 may be stepped by 40 µm so that the focal points of the optical radiation through each of these fibers are spaced apart. However, a step spacing other than 40 µm may also be used.

Referring now to FIG. 3, A-scans for each of the multiple single mode fibers 10, in the fiber bundle tip 12, are acquired over approximately the entire 2 mm imaging depth, but retained only over a short axial range of approximately 40 µm near the focal point of each fiber where the beam diameter is close to a minimum (indicated at 34) and does not vary substantially with axial position. This range of 40 µm, in this exemplary design, is indicated at 31. The A-scans are performed simultaneously by each of the multiple single mode fibers 10 within the fiber bundle tip 12. Effectively, the multiple A-scans cover the entire depth of 2 mm in the sample tissue at different radial directions, but for each of the multiple single mode fibers 10, only sections of the respective A-scan in a corresponding 40 µm depth-of-focus 31 are used to build up the image. As shown in the focal zone 31, each of the beams 21b, 22b and 23b show a distinct "hourglass" shape for the focal points 38, 37 and 36, in known manner. For each of the beams 21b, 22b and 23b, the far field beam spread is indicated by lines 32 and the near field beam spread is indicated by lines 34.

The purpose of rotating the mirror 16 is to create radial (i.e. lateral) scans in a direction that is perpendicular to the A-scan direction to create a B-scan image, i.e. the scan area 28 of FIG. 1. The resultant radial scan pattern of the focal points of the individual fibers from the multiple single mode fibers 10 is illustrated in FIG. 4. It is worth noting that a continuous scan surface is only present when the cleaved face of the mirror 16 is faced substantially in the direction of locations "A" and "C", where B-scan images should be taken. At other locations on the radial scan pattern, a "dead space" between the individual A-scans is too large to allow for sufficient sampling of the tissue. Therefore, the present invention comprises a sector-scan imaging device, to scan a sector substantially in the "A" or "C" locations, with a sector angle of about 20°, within which a 2 mm by 2 mm image is obtained. In this example, with the given geometry, a larger sector angle will produce "dead spaces" which are too large to form a suitable cross-sectional image.

FIGS. 4b and 4c show beam focal points 36, 37 and 38 from both a top view and an end view respectively. As shown, and corresponding to earlier figures, the individual focal points 36, 37 and 38 are spaced apart in the radial plane perpendicular to the axis 20. As FIG. 4c shows, in an end view along the axis 26, the focal points 36, 37 and 38 are spaced apart in terms of depth but overlap to create a continuous scanning surface or scan area 28.

If, the cleaved face of the mirror 16 is faced substantially in the direction of the locations indicated at "B" and "D", in FIG. 4a, which is perpendicular to the scanning surface or scan area 28, then the patterns shown in FIG. 4d (a top view of the pattern) and FIG. 4e (a sideview of the pattern) are obtained. Here, the focal points are indicated at 40, 41 and 42. As shown in FIG. 4d, the focal points 40, 41 and 42 are each in an individual plane 40', 41' and 42' which are spaced apart corresponding to the spacing of the fibers in the fiber bundle tip 12. The planes 40', 41' and 42' are perpendicular to the axis 20. In FIGS. 4b to 4e, arrows 44 indicate the direction of the radial scan.

For the linearly translated system shown in FIG. 1d, there are no "dead spaces" and thus linear translation can produce images suitable images approximately 2 mm by 2 mm in size.

In the exemplary design of the endomicroscopic system, the maximal speed of tissue motion, due to physiological motion, was chosen as 5 mm/s for in vivo imaging. A near diffraction-limited focusing lens (i.e. a lens which approximates an ideal lens by providing very small focal points) was chosen as the focusing lens 14. The near diffraction-limited focusing lens was supplied by Melles Griot Inc. In addition, each single mode fiber, from the plurality of single mode fibers 10, had a core diameter of 5 microns (i.e. $\emptyset_c \approx 5$ μm) and was operated at a wavelength of 0.86 μm. Furthermore, the design incorporates an approximate core index of $n_c=1.447$ and a difference in the refractive index between the core and the cladding of $\Delta n=0.005$. Using these values, the NA of the fiber is then given by:

$$NA \approx n_c(2\Delta n)^{1/2} = 0.145 \qquad (1)$$

and the acceptance angle, $\theta_a$, of the fiber is given by:

$$\theta_a = \sin^{-1}(NA) = 8.32° = 0.145 \text{ rad} \qquad (2)$$

The design further incorporates the concept of an ideal lens which is used to focus optical radiation, from the plurality of single mode fibers 10, at a magnification of 1 to 1 and that the far field beam divergence angle is similar to $\theta_a$. Then, for light beam radiation with a center wavelength $\lambda_o$, the beam diameter at the focal point is given by:

$$\emptyset_f = 2w_o = 2\frac{\lambda_0}{\pi\theta_a} = 3.95 \text{ μm} \approx \emptyset_c \qquad (3)$$

The spot diameter $\emptyset_f$ is approximately equal to the core diameter ($\emptyset_c=5$ μm) which results in efficient optical coupling. The depth of focus is $$2\frac{\pi w_0^2}{\lambda_0} = 27.2 \text{ mm}$$

and the beam diameter at the ends of the focal zones for focal points 36, 37 and 38 is given by:

$$\emptyset_f' = 2\sqrt{2}w_0 = 5.59 \text{ mm} \qquad (4)$$

Since the $\emptyset_f$ and $\emptyset_f'$ parameters are defined in terms of amplitudes, within 40 μm of the focal point in the axial direction, the beam diameter based on light intensity (i.e. the square of the light amplitude) may actually be smaller than 5 μm.

The above calculation is based on ideal optics operating on the principle optical axis. Using an off-the-shelf lens system with $\emptyset=5$ mm, $f=5$ mm, and a working distance of 8.2 mm, it has been found that the off-axis angle required to cover a 2 by 2 mm image is about 5° using commercial ray-tracing software. At approximately an 80% fill factor of the focusing lens 14, the ray-tracing results show the on-axis RMS focal point to be 5.3 μm in radius, and the 5° off-axis RMS focal point to be 10.3 μm in radius. A custom designed lens system should have better performance.

As illustrated in FIG. 1, the working distance of the entire optical system, i.e. the distance from the focusing lens 14 to the focal point of the apparatus is determined by the focal length of the lens system, the diameter of the focusing lens 14 and the gap between the focusing lens 14 and the mirror 16. Using the off-the-shelf lens system discussed above, the working distance is about 2.35 mm. The distance from the center of the image to the rotational axis of tie mirror 16 is about 5.47 mm. To obtain a 2 mm scan in the radial direction, the sector scanning angle should be approximately ±10.4°, or about 20° in total, as determined by the geometry of the optical system.

Currently existing in vivo OCT systems perform radial scans at 4 to 8 revolutions per second (RPS) to yield a biologically acceptable 4 to 8 frames per second. For the design of the present embodiment, 4.4 RPS is chosen as the rotational speed. The rotational speed depends on the repetition rate of the A-scans and the number of A-scans required to obtain a 5 μm lateral resolution. Therefore, the imaging speed of the apparatus of the present invention is 4.4 frames/s while other imaging speeds may be chosen based on different end-user applications. The imaging time for each individual frame is 12.6 ms, as determined by the rotation speed and the sector scanning angle. Therefore, for a given frame, the system is acquiring signals for 12.6 ms and the time between frames is about 215 ms during which data processing is performed. These parameters are dependent on the performance of the optical delay generator (which is described later) that is used in the system.

Figure 5B:
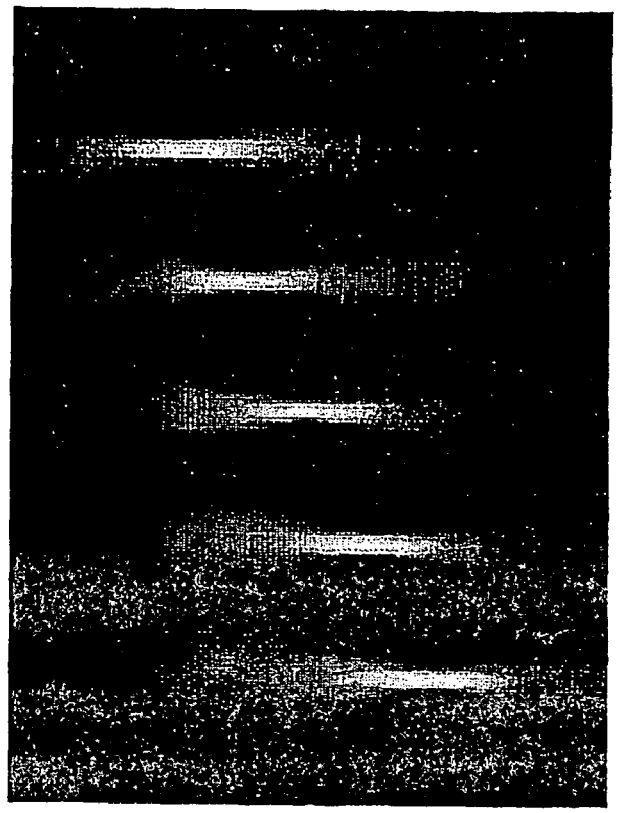
FIG. 5b is a beam spot diagram of 5 central channels of a 15 channel fiber bundle tip showing electric field strength distribution near multiple focal zones.
Figure 5A:
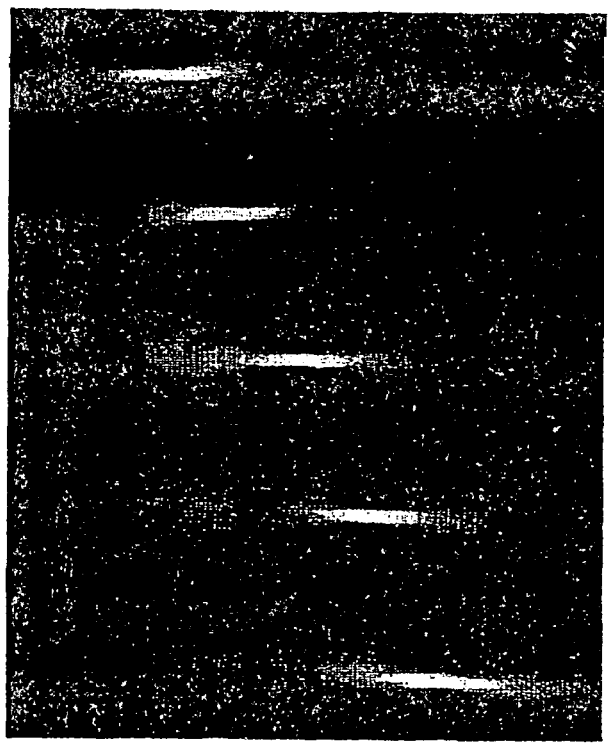
FIG. 5a is a beam spot diagram of a 5 channel fiber bundle tip showing electric field strength distribution near multiple focal zones.

While the above calculations were made based on a light source operating at a light wavelength of 860 nm and custom made single mode fibers, implementation using a light source operating at other wavelengths, such as 1300 nm, and off-the-shelf fiber may also be possible. FIG. 5a shows a beam spot diagram for a 5 channel fiber bundle tip operating at a wavelength of 1300 nm and using off-the-shelf fibers (Corning SMF-28). The fiber bundle tip has a fiber step size of 125 μm. The light beams from these fibers, focused by a lens having a 5 mm diameter and a 4.5 mm focal length, cover a focal zone of approximately 0.65 mm. The resulting lateral imaging resolution is approximately 10 μm. FIG. 5b shows a beam spot diagram for a 15 channel fiber bundle tip operating at a wavelength of 890 nm and using custom designed fibers having a core diameter of 5 μm and a cladding diameter of 40 μm. This fiber bundle tip has a fiber step size of 40 μm. The beams spots of only the central 5 resulting lateral imaging resolution is approximately 5 μm over a focal zone of approximately 0.65 mm.

Figure 5D:
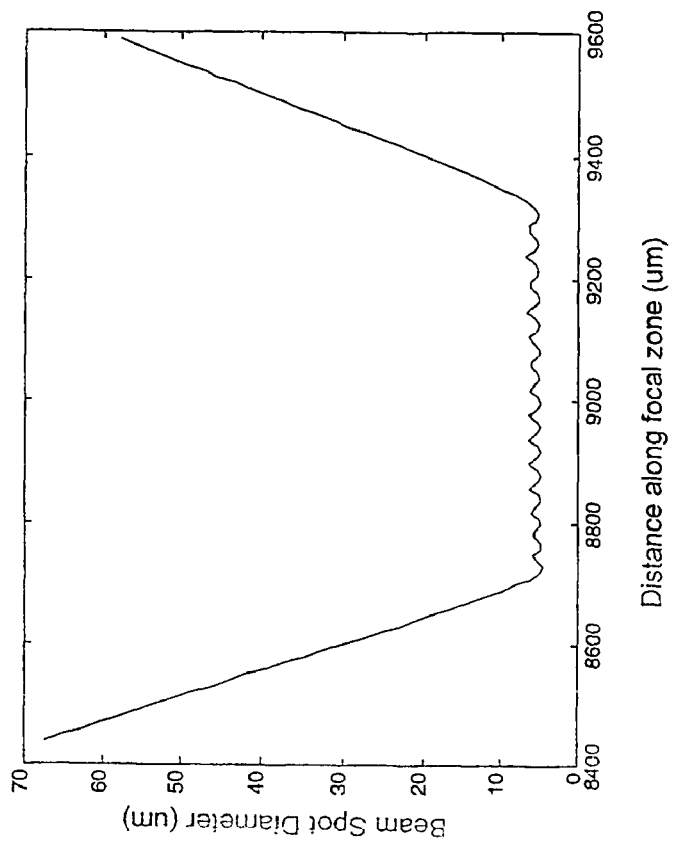
FIG. 5d is a graph of beam spot diameter versus focal zone distance for the fiber bundle tip of FIG. 5b.
Figure 5C:
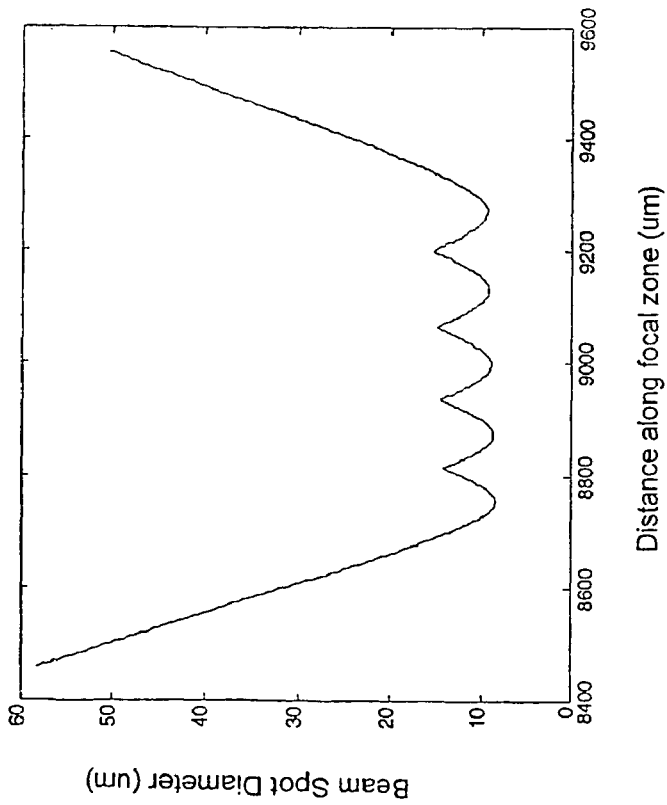

FIG. 5c shows beam spot diameter versus distance along the focal zone for the 5 channel fiber bundle tip of FIG. 5a. FIG. 5c shows that the beam spot diameter is consistently less than 15 μm over the entire 0.65 mm focal zone. FIG. 5d shows beam spot diameter versus distance along the focal zone for the 15 channel fiber bundle tip of FIG. 5b. FIG. 5d shows that the beam spot diameter is approximately 5 μm over the entire 0.65 mm focal zone.

Figure 6:
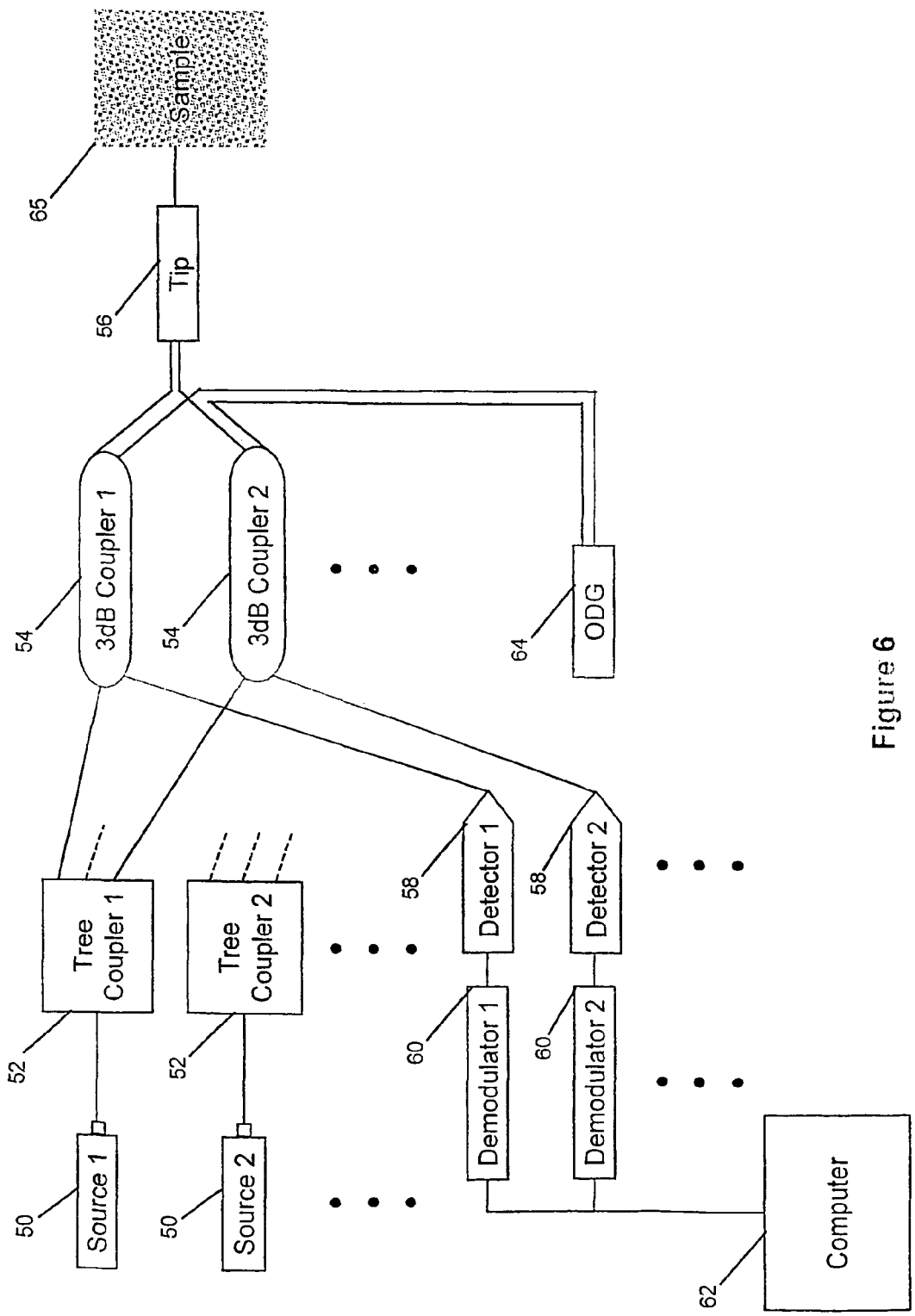
FIG. 6 is a schematic layout of an apparatus in accordance with the present invention.

Referring now to FIG. 6, the overall general layout of the basic optical elements of the apparatus of the present invention comprises a plurality of optical sources 50, a plurality of tree couplers 52, a plurality of 3 dB couplers 54, a fiber bundle tip 56, a plurality of detectors 58, a plurality of demodulators 60 and an optical delay generator 64. The plurality of optical sources 50, which may be lasers, are connected to the plurality of tree couplers 52. More than one laser may be needed to ensure that adequate optical radiation is provided to each of the fibers (i.e. channels) in the tip 56. Each tree coupler 52 couples a respective optical source 50 to a subset of the plurality of 3 dB couplers 54. The plurality of 3 dB couplers 54 are connected to the fiber bundle tip 56 for onward transmission of approximately half of the light radiation from the plurality of optical sources 50. The fiber bundle tip 56 includes fiber bundle tip 12 and the other optical elements of FIG. 1 (i.e. the focusing lens 14 and the mirror 16). The other half of the radiation from the plurality of optical sources 50 is reflected back to detectors 58 which in turn are connected through the demodulators 60 to a computer 62 which functions to process the sampled data to generate the B-scan image 30. The optical delay generator 64 is used by the 3 dB couplers 54 to provide a delayed reflected signal to the detectors 58. The sample being investigated by the tip 56 is indicated at 65.

In the layout shown in FIG. 6, 1 dB or 10 dB optical couplers and the like may be used in place of the 3 dB couplers 54. Furthermore, the intensity of the optical radiation transmitted to each of the 3 dB couplers 54, and consequently each fiber, by the tree couplers 52 need not be the same and in fact is chosen depending on whether the 3 dB coupler provides optical radiation to a fiber (i.e. channel) that facilitates a deep or shallow scan into the tissue. High intensity optical radiation is needed to scan deeply into the tissue. Accordingly, tree couplers 52 and 3 dB couplers 54 that feed optical radiation to fibers that scan deeply into the tissue are adapted to provide larger amounts of optical radiation.

Figure 7A:
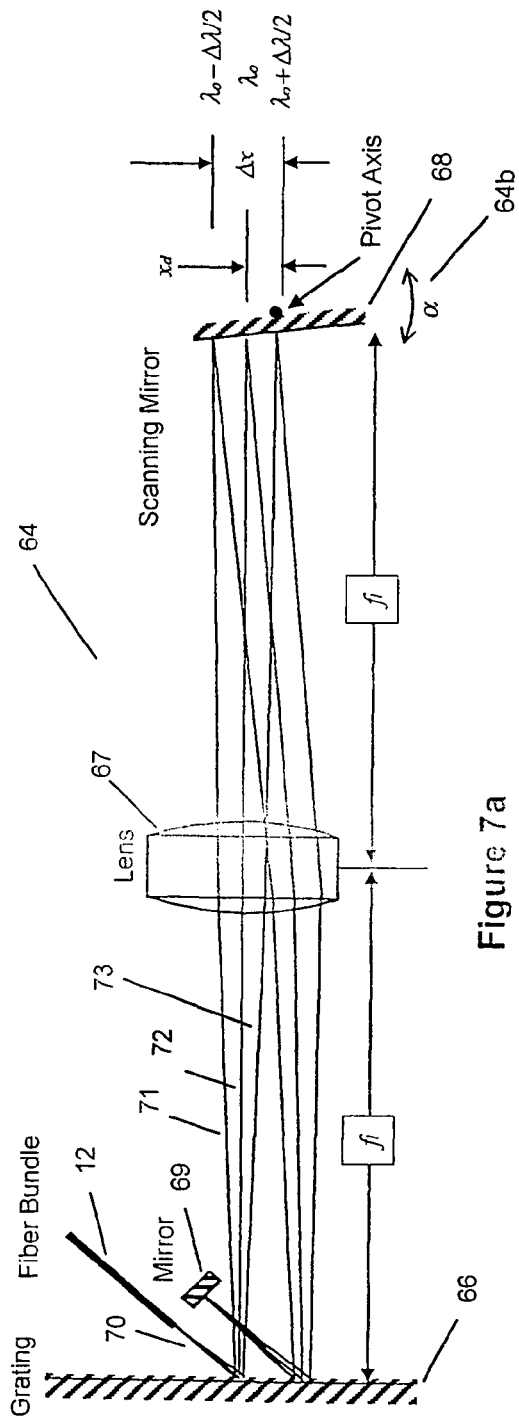
FIG. 7a is a top view of an optical delay generator used in the apparatus of the present invention.
Figure 7B:
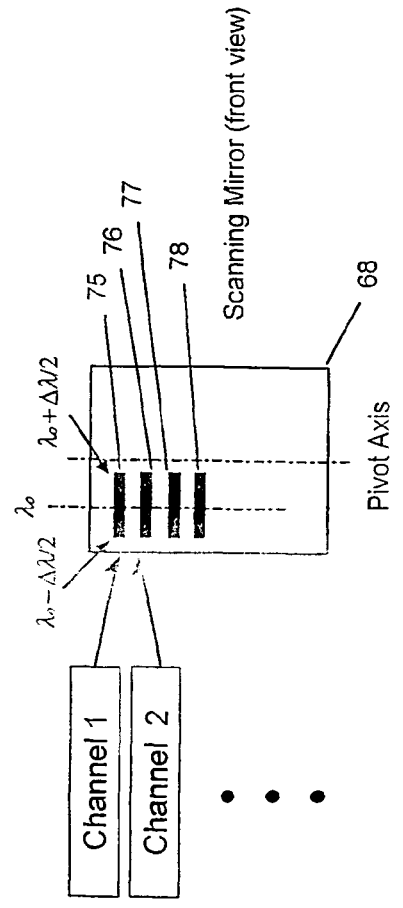

FIGS. 7a and 7b show the optical delay generator 64 in greater detail. The optical delay generator 64, similar to those in existing in vivo OCT systems, is used to perform the A-scans using the coherence envelope of each individual fiber. The optical delay generator 64 comprises a grating 66, a lens 67, a scanning mirror 68 and a mirror 69. Rapid depth scanning can be achieved with the optical delay generator 64 by dispersing quasi-monochromatic light from the multiple single mode fibers 10 in the fiber bundle tip 12 onto the diffraction grating 66 and focusing the dispersed light onto the oscillating mirror 69. This has the effect of applying a linear ramp in the frequency or Fourier domain as described by G. J. Tearney, B. E. Bouma and J. G. Fujimoto ("High-speed phase and group delay scanning with a grating based phase control line" Nature Medicine 4(7), 861–865 (1998)). With recombination of the reflected wavelengths at the diffraction grating 66, a real space-time delay is created. The angle of the scanning mirror 68 is rapidly oscillated through several degrees of rotation creating a rapidly varying time delay in the reference arm which allows for fast, repeated depth scanning of a sample.

The optical radiation 70 from one fiber from the multiple single mode fibers 10 is shown in FIG. 7a. The optical radiation 70 is dispersed into spectral components represented by spectral components 71, 72 and 73 by the grating 66. Spectral component 71 represents the lowest wavelength in the optical radiation 70; spectral component 73 represents the highest wavelength in the optical radiation 70; and spectral component 72 represents the center wavelength in the optical radiation 70. These spectral components of the optical radiation 70 are vertically aligned in the optical delay generator 64. In a similar fashion, optical radiation from other fibers from the multiple single mode fibers 10 are dispersed and vertically aligned, with a vertical spacing between the dispersed optical radiation from the different fibers. The offset of the center wavelength of the dispersed optical radiation from the pivot axis of the scanning mirror 68, for a given fiber, is represented by $X_d$ which facilitates phase modulation of the dispersed optical radiation from each of the multiple single mode fibers 10. Alternatively, if $X_d$ were zero then a phase modulator would be needed, for each of the single mode fibers 10, to phase modulate the optical radiation from each of the single mode fibers 10. This has the advantage of allowing for a reduction in size of the scanning mirror 68 which in turn allows for a higher frame rate to be used. Furthermore, the phase modulator is electrically controlled which allows for very stable signals are generated Referring now to FIG. 7b, the multiple single mode fibers 10 are aligned in the fiber bundle tip 12, such that dispersed optical radiation from each of the multiple single mode fibers 10 is vertically aligned on the scanning mirror 68 as rows 75, 76, 77 and 78. Alternatively, other ordered arrangements may also be used for the spectral components of the optical radiation from each fiber from the multiple single mode fibers 10 such as columns.

As illustrated in FIG. 6, a single optical delay generator may be used to introduce delay in multiple fibers. The limiting factor in determining the number of channels that may be coupled to a single optical delay generator is the physical size of the scanning mirror which is in turn limited by the resonance frequency of the optical delay generator. Commercially available resonance optical scanners can operate up to 16 kHz. Accordingly, a size of 4 mm by 5 mm may be used for the scanning mirror 68. Since the fiber bundle array is about 2 mm in size, it is possible to fit the entire array onto one optical delay generator. Therefore, for the embodiment of the present invention, a single optical delay generator is used having an optical scanner operating at $f_r$=16 kHz with an optical scan angle α of ±2°. The embodiment also incorporates a grating pitch of p=3.33 μm, a center wavelength of $\lambda_0$=0.86 μm and a focal length of $f_1$=21 mm. Accordingly, the free space group path length difference $\Delta l_g$ is given by (from Rollins et al. 1998):

$$\Delta l_g = 4\alpha \left( f_1 \frac{\lambda_0}{p} x_d \right) = 0.618 \text{ mm} \quad (5)$$

which is also 1.24 mm peak to peak. In equation 5, $x_d$=1 mm is the displacement between the $\lambda_0$ spectral line and the pivoting axis on the resonance mirror. The peak A-scan speed is given by:

$$V_{Amax} = 2\pi \Delta l_g f_r = 62.1 \, m/s \quad (6)$$

and the A-scan speed varies according to equation 7.

$$V_A = V_{Amax} \cos(2\pi f_r t) \quad (7)$$

Choosing a source with a coherence length $l_c$ of 5 μm and a Gaussian emission spectrum, the equivalent emission bandwidth is given by:

$$\Delta \lambda = \beta \frac{\lambda_0^2}{l_c} = 98 \text{ nm} \quad (8)$$

where b=0.66 for a Gaussian envelope.

The size of the resonant mirror is determined next. For an optical delay generator with a grating having a first order diffraction, the diffraction angle is given by:

$$\theta(\lambda) = \sin^{-1}(\lambda/p) \quad (9)$$

The spread of the spectrum from $(\lambda_0 - \Delta\lambda/2)$ to $(\lambda_0 + \Delta\lambda/2)$ at the Fourier plane of the lens is given by:

$$\Delta x \approx 2 f_1 [\theta(\lambda_0 + \Delta\lambda/2) - \theta(\lambda_0 - \Delta\lambda/2)] = 1.3 \text{ mm} \quad (10)$$

Since the mirror width is 4 mm, one can fit the spectrum on one side of the resonant mirror with the displacement $x_d$ having a value of approximately 1 mm. This is illustrated in FIGS. 7a and 7b. The carrier frequency of an individual channel of the system is given by (Rollins et al. 1998):

$$f_c = (4x_d \alpha 2\pi f_r / \lambda_0) \cos(2\pi f_r t) \quad (11)$$

which is 16.3 MHz at the maximum.

The bandwidth of the interferogram (i.e. the interference fringe pattern) is given by:

$$\Delta f = \frac{\Delta \lambda}{\lambda_0^2} 4\pi \alpha f_r 2(f_t \lambda_0 / p - x_d) \cos(2\pi f_r t) \quad (12)$$

which is 8.4 MHz at the maximum.

Since $f_c(t) > \Delta f(t)$, proper demodulation can be performed by conventional rectifying and low-pass filtering, although a sharp frequency cut-off is needed. It is preferable to set up the individual channels of the system such that $D_A = 40$ μm (the depth of the A-scan performed by a single channel) coincides with the maximum carrier frequency, so that the variation in carrier frequency over $D_A$ is minimized. The carrier frequency varies sinusoidally in time given by:

$$\Delta f_c = f_c \{1 - \cos[\sin^{-1}(D_A |\Delta|_g)]\} = 34 \text{ kHz} \quad (13)$$

which is about 0.2% of $f_c$.

At other locations, the signal can still be properly demodulated, but the variation in carrier frequency will be larger. The demodulators 60 may incorporate an analog high-speed rectifier and a 10-pole low-pass filter to demodulate the signal. Effectively, the signal is frequency down-shifted such that the signal is centered at DC and has a bandwidth of Δf. The demodulated envelope signal is then digitized at an appropriate sampling rate. Current existing data acquisition (DAQ) cards operate at 30 MegaSamples per second (MS/s) with an SNR of about 60 dB. Choosing a Gaussian shape for the interferogram spectrum with Δf=8.4 MHz, the 60 dB point is at about 14.5 MHz. Accordingly, the Nyquist rate for digitizing such a signal is approximately 29 MS/s. Therefore, current existing DAQ cards will be able to digitize the envelope signal without aliasing.

Given a sampling rate of 30 MS/s for digitizing the envelope signal at the maximum carrier frequency, the spatial sampling interval in the axial direction is: $\Delta_{axial} = V_{Amax}/S = 2.07$ μm. As shown in FIG. 8, a scan path 80 is indicated showing A-scans alternately going up and down through the sample. Sampling points are indicated at 82. The axial spacing of 2.07 μm is indicated at 84. The spatial sampling interval in the lateral direction is determined by the lateral or B-scan velocity and the resonant frequency of the optical scanner in the optical delay generator 64. At the center of the image, where the radial distance r is 5.47 mm from the rotational axis of the mirror, the radial sampling interval is given by:

$$\Delta_{radial} = V_{radial}/2f_r = 2\pi \Omega r / 2f_r = 4.73 \text{ μm} \quad (14)$$

This interval is indicated at 86 in FIG. 8. For the fiber scanning the shallowest depth, the spatial lateral sampling interval is 3.86 μm and for the deepest channel it is 5.59 μm. Therefore, the pixel size at the center of the image is 2.07 by 4.73 μm in the axial and lateral direction respectively. The lateral pixel size varies across the depth of the image from 3.86 to 5.59 μm. By varying the rotational speed of the mirror 16, the lateral sampling interval can be changed, at the expense of frame rate. If a higher resonance frequency optical scanner is used, the sampling interval may also be reduced.

For a pulsed optical source (e.g. a 15 to 20 fs pulsed laser emitting light with a wavelength of 860 nm), the coherence length will be approximately 4.5 to 6 μm. Since the spatial sampling interval in the axial direction is about 2 μm, which is smaller than half of the coherence length, the image is reasonably sampled in the axial direction. Using a near diffraction-limited focusing lens as the focusing lens 14, the beam spot size should be about 5 μm. Since the spatial sampling interval in the lateral direction varies from 3.86 to 5.59 μm, the image is slightly under sampled, given that the beam waist size is about 5 μm. However, the spatial sampling interval is not equivalent to the final image resolution, which is also influenced by local contrast and noise levels. Local contrast is the difference in reflectivity between two points in the sample that show up as adjacent pixels in the image. If the two points have similar reflectivity, i.e. low local contrast, it will be difficult to resolve these points.

Imaging speed should be fast enough to reduce motion blurring. Given that the target speed (i.e. tissue motion) is typically 5 mm/sec, then within a frame time (an elapsed time of 12.6 ms), the target can move up to 63 μm in a particular direction which is much larger than the designed 5 μm resolution. In the present embodiment, the A-scan is performed simultaneously in all channels such that one line of the image is formed within 0.6 μs which is the time required to scan the coherence gate through a 40 μm distance. The time between two consecutive A-scans is about 16 μs, which is determined by the rotational speed of the mirror 16 of the system and the number of A-scans per image. Thus, the resultant image should be crisp since the motion during 16 μs is 0.08 μm which is much less than the resolution. Accordingly, there should be no motion blurring in the image but a motion artifact may still exist. The resultant motion artifact may be a geometric deformation of the features being imaged that may be as large as 63 μm depending on the size of the feature and the target velocity. This motion artifact is due to the effect that the air-tissues interface has on the optical radiation from the plurality of optical sources 50.

Figure 9:
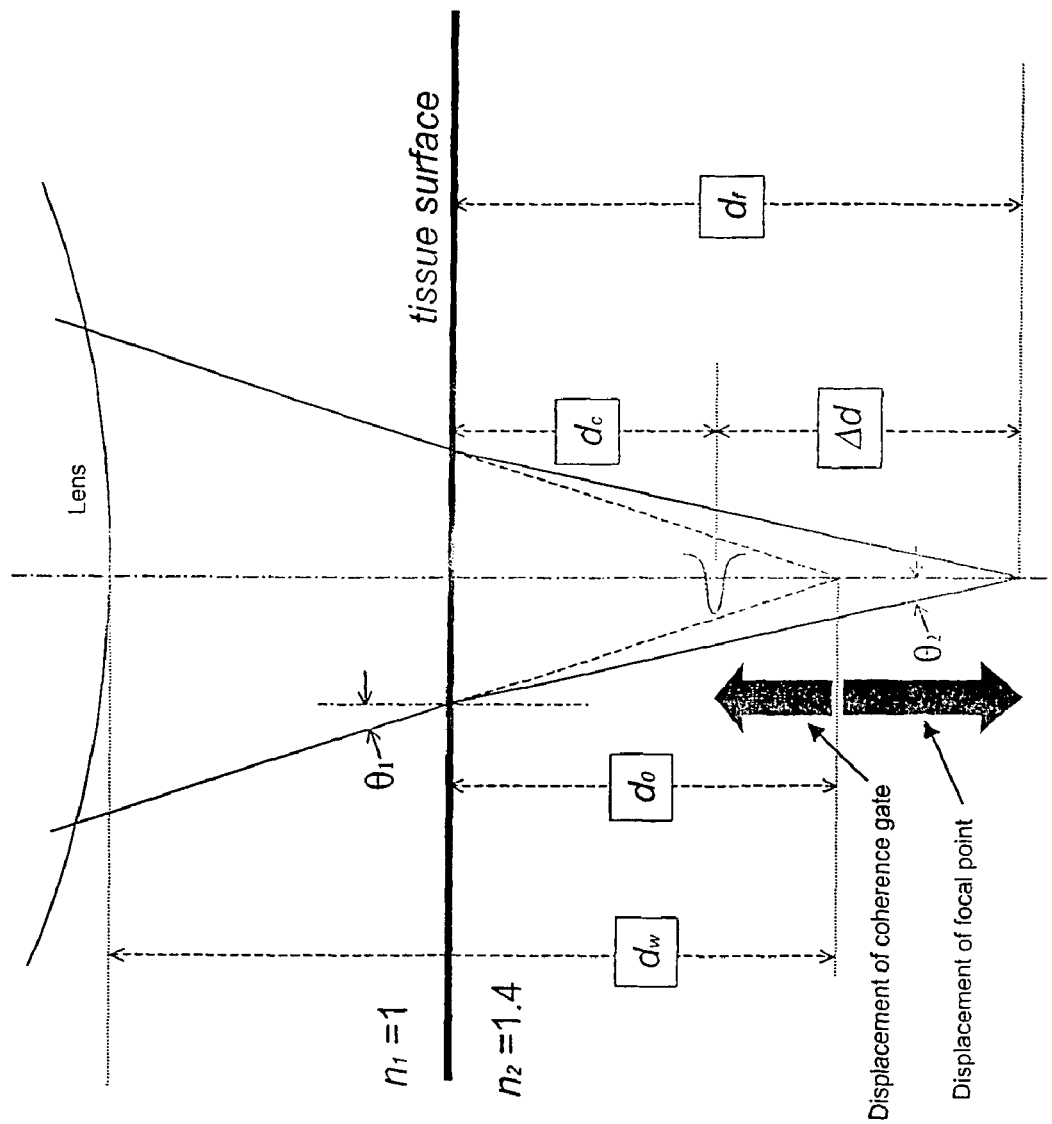
FIG. 9 is a diagram illustrating mismatch between the coherence gate and the focal point due to the air-tissue interface for light radiating from a single imaging fiber of the present invention.

As illustrated in FIG. 9, the focal point of an individual fiber of 30 the apparatus, inside the tissue being imaged, can vary depending on the distance $d_0$ of the location of the focal point in the tissue, whether the tissue surface had a refractive index of 1, and the actual refractive index of the tissue (which is typically approximately 1.4). Accordingly, the actual focal point is at a distance df below the tissue surface given by:

$$d_f = d_0 \frac{\tan \theta_1}{\tan \theta_2} = d_0 \frac{\tan \theta_a}{\tan \left[ \sin^{-1}\left( \frac{n_1}{n_2} \sin \theta_a \right) \right]} \quad (15)$$

where $\theta_1$ is assumed to be equal to $\theta_a$, the acceptance angle of the individual fibers and $\theta_2$ will be determined by the refractive index $n_1=1$ (i.e. air) outside the tissue and $n_2=1.4$ inside the tissue.

The coherence gate location varies according to:

$$d_c = \frac{n_1}{n_2} d_0 \quad (16)$$

Accordingly, due to the fact that optical radiation travels more slowly in a medium with a larger refractive index there is an optical path mismatch between the focal point and the coherence gate of an optical beam which is matched in a medium with $n_1=1$ (i.e., with no tissue present). This mismatch is:

$$\Delta d = n_2(d_f - d_c) = \frac{n_2 d_0 \tan\theta_a}{\tan\left[\sin^{-1}\left(\frac{\sin\theta_d}{n_2}\right)\right]} - d_0 \quad (17)$$

A tissue refractive index of $n_2=1.4$ yields $\Delta d=0.97\ d_o$. This mismatch problem is common for all high-NA OCM systems and many existing high-NA OCM systems use some form of dynamic compensation, i.e., changing the reference path length dynamically to compensate for $\Delta d$, however, such dynamic compensation is difficult with a high imaging speed. Accordingly, one aspect of the embodiment of the present invention is to use 'flexible triggering' of the detected interferogram signal.

As shown above, the free space group path length difference is $2\Delta l_g=1.24$ mm peak to peak, which is much larger than the useful A-scan range of only 40 μm. This leaves room for dealing with the mismatch since one then can trigger to obtain the interferogram only when the coherence gate is passing through the focal point.

As shown in FIG. 9, the working distance for each fiber channel, $d_w$, varies with $n_2$ which is approximately constant Therefore, if one knows where the tissue surface is, $d_0$ can be determined and in turn $\Delta d$ can be determined.

Figure 10:
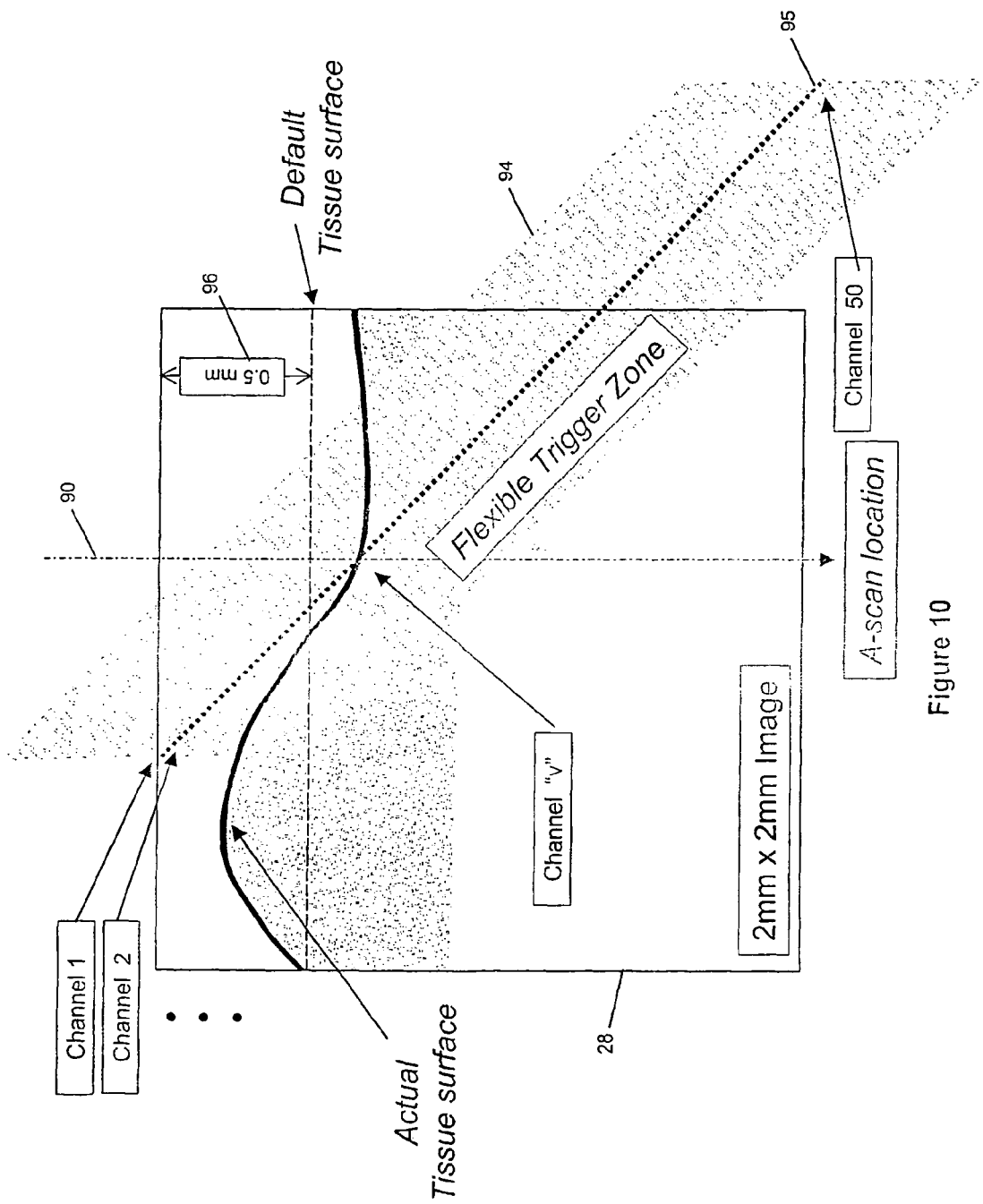
FIG. 10 is a diagram illustrating flexible triggering of the apparatus of the present invention to accommodate the mismatch shown in FIG. 9.

Referring to FIG. 10, showing a perspective view of a tissue surface and an arbitrary axial line 90, channel 1, which is designated to scan the surface of the tissue, is the first to pass through the axial line 90, in the scan area 28. The focal points of channels 1 and 2 are indicated at 91 and 92 in a schematic representation 94 of the optical radiation from the multiple single mode fibers 10 (i.e. channels) passing through the axial line 90. The focal point of the last channel, i.e. channel 50 in this example, is indicated at 95 and is designated to scan the deepest layer of the tissue in the image. The overall profile of the representation 94 defines a flexible trigger zone, within which the coherence gate and the focal length can be matched. One of the 50 channels, i.e. channel "v", will experience a large and distinctive specular reflection since the air-tissue interface approximates a mirror and reflects incident light. Underneath the tissue surface, the tissue acts as a turbid media which scatters and absorbs incident optical radiation. Thus, channel "v" will determine $d_0$ for this particular axial line 90 since all of the channels before channel "v" will return a signal that is at noise level. Accordingly, the "flexible triggering" method comprises comparing the detected reflected optical radiation for adjacent channels to locate the tissue surface by identifying the channel in which there is a large increase in reflectance compared to its 'neighboring' channels. This information is then passed on to each of the subsequent channels and the trigger point for each channel is set accordingly to reduce mismatch between the focal point and the coherence gate.

As an example, if channel "v" is channel 13 then the apparatus is calibrated such that channels 1 to 12 are set to scan free space above the tissue surface, channel 13 to scan the tissue surface, and subsequent channels are set to scan deeper tissue, with no mismatch between the focal point and the coherence gate of the optical beam of each channel. During imaging, a tolerance of $\Delta d_o=\pm 0.5$ mm of the location of the tissue surface can be allowed as indicated at 96 in FIG. 10. This tolerance is related to the A-scan performance and the frequency response of the envelope detector as will now be explained.

Given $\Delta d_o=0.5$ mm, the mismatch that needs to be compensated for is given by:

$$\Delta d'=0.693\times 0.5=0.347\ \text{mm} \quad (18)$$

This means that instead of triggering the interferogram signal at the maximum carrier frequency, the actual carrier frequency needs to be:

$$f_c'=f_{cmax}\cos(\sin^{-1}(\Delta d'/\Delta l_g))=13.5\ \text{MHz} \quad (19)$$

which is about 83% of the maximum carrier frequency with the interferogram signal bandwidth changing accordingly. Although the envelope detector's frequency response can be tuned dynamically, it is simpler and faster for the envelope detector to have a fixed response but it was designed for a 17% tolerance of the cut-off frequencies. In this way, the entire flexible triggering scheme contains only fixed components and all of the compensation is performed electronically to satisfy the high imaging speed requirement.

The optical components show in FIG. 6 can be chosen as follows. Based on Boppart, S. A., Bouma, B. E., Pitris, C., Southern, J. F., Brezinski, M. E., and Fujimoto, J. G. (In vivo *Cellular Optical Coherence Tomography Imaging*, Nature Medicine, Vol. 4-No.7:861–865, July 1998), an SNR of greater than 100 dB can be achieved in a non-endoscopic OCT system using 2 mW of incident power on the tissue to allow for imaging to a depth of approximately 2 to 3 mm. The optical source used was a Kerr-lens mode-locked solid-state $Cr^{4+}$: forsterite laser operating at a 1280 nm center wavelength with a coherence length of 5.1 μm. However, the embodiment of the present invention is not limited to this type or any other particular type of source, such as a broadband superluminescent diode. For instance, another possibility is a white-light emission Cr:LiSAF optical source with a bandwidth of approximately 100 nm centered at 860 nm which will provide a coherence length of approximately 4.5 to 6 μm. This diode-pumped, solid-state, mode-locked laser should operate with a pulse-repetition rate of about 100 MHz and an average power of 30 mW when operated at 860 nm. The pulse energy variation should be less than 1%. Several (e.g., 2 or 4) of these lasers as indicated at 50 in FIG. 6 are needed to provide the total power requirement of the 50 channels. The channels scanning the deeper portion of the tissue will need about approximately 1 to 2 mW of incident power per channel and the channels scanning the shallower portion will need less. The tree couplers 52 can be configured to split the source power to match these requirements. Since the maximum carrier frequency is 16.3 MHz, each interference fringe will contain at least 6 laser pulses. Therefore the fringe pattern should be adequately sampled.

For each channel, a separate photo receiver or detector 58 may be used to detect the interference fringes. The maximum detector bandwidth is 125 MHz, although in the apparatus of the present invention, a detector bandwidth of 30.8 MHz may be sufficient, as determined by the carrier frequency and the bandwidth of the interferogram.

Figure 11A:
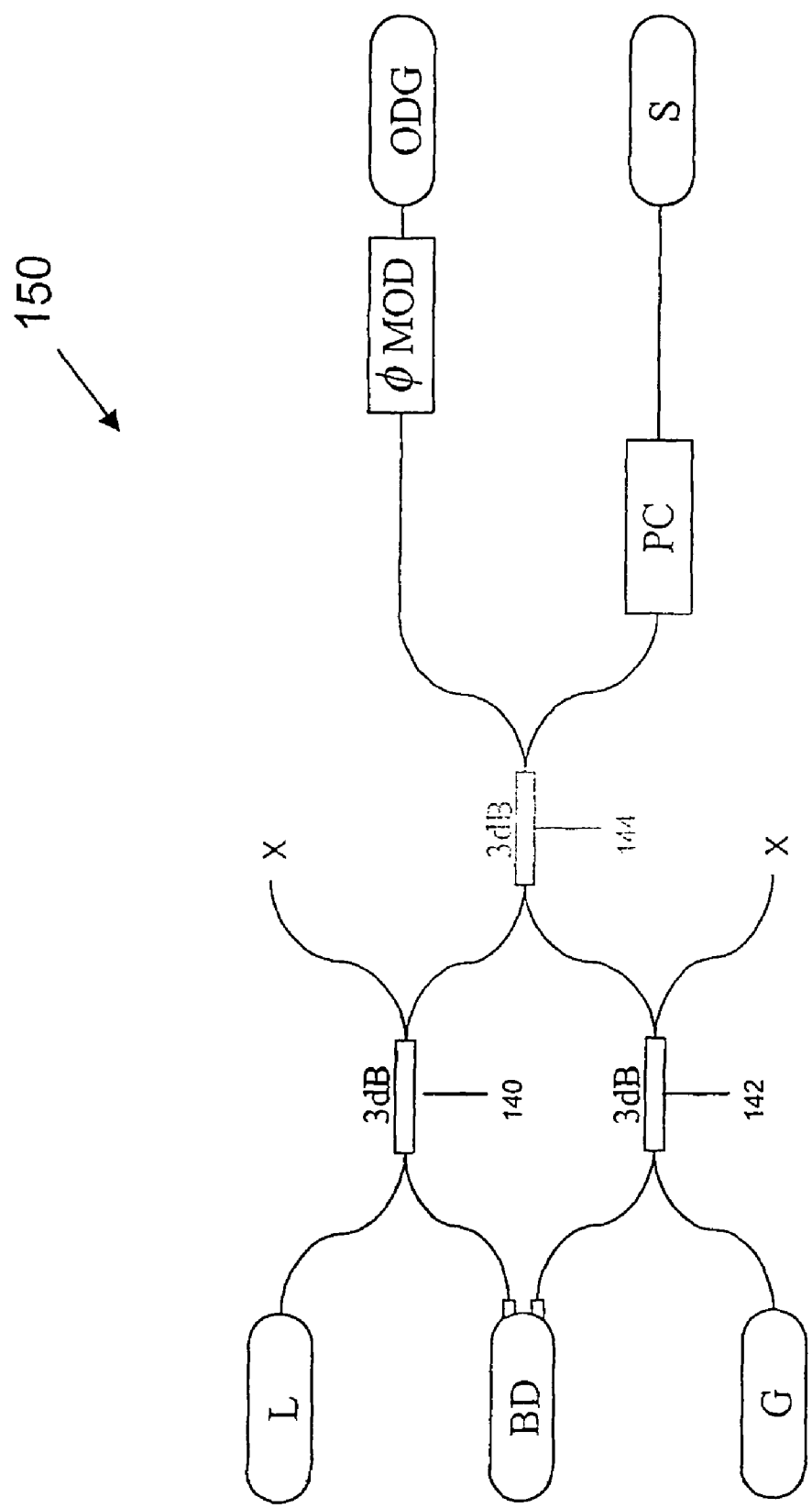
FIG. 11a is a schematic diagram of a Prior Art single channel Optical Coherence Tomography device.

An alternate embodiment of the present invention involves the concept of sharing optical components to reduce device complexity and cost. Referring to FIG. 11a, a typical single channel interferometer 150 with balanced detection in which the AC component of the interferogram is separated from the DC component of the interferogram and only the AC component is amplified is shown. The single channel interferometer 150 comprises an IR broadband light source L, a visible wavelength guide light G, a balanced detector BD, a polarization controller PC, a phase modulator φMOD and an optical delay generator ODG which are connected through a network of optical fibers and 3 dB couplers 140, 142 and 144. The "x" denotes a dead end in the fiber network. The visible wavelength guide light G may be a green laser which indicates the direction in which the single channel interferometer 150 is pointing (i.e. it indicates what will be imaged). The single channel interferometer 150 is connected to a sample S.

Figure 11B:
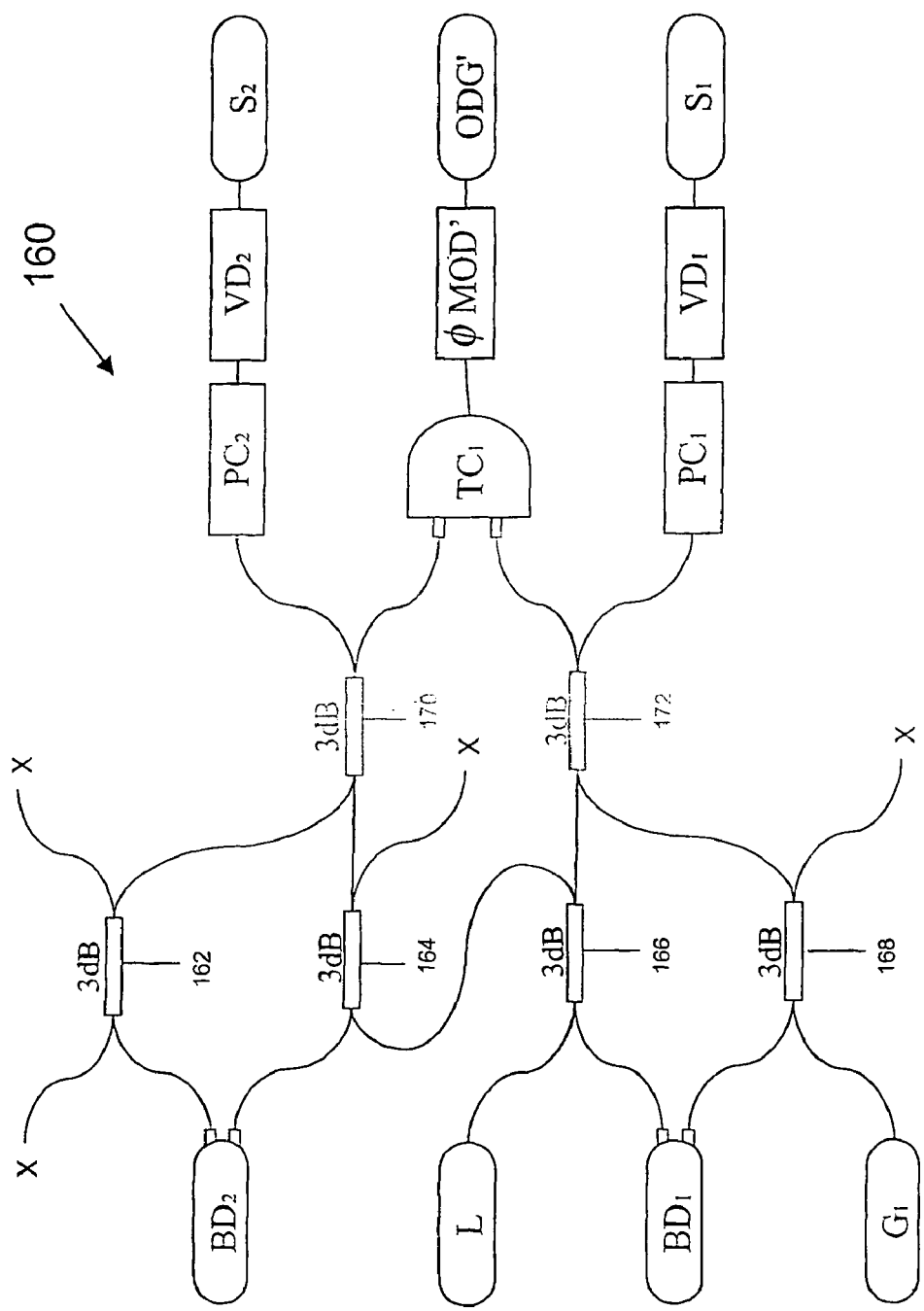
FIG. 11b is a schematic diagram of a two channel Optical Coherence Tomography device.

The design of FIG. 11a can be extended to construct a two channel interferometer 160 as shown in FIG. 11b. The subscripts denote the components that are in the two channels. A component without subscripts indicates that the component is used in both channels. The two channel interferometer 160 comprises a laser L', a visible wavelength guide laser G', a 2 to 1 tree coupler TC1, polarization controllers $PC_1$, $PC_2$ and phase modulator φMOD', variable delay elements $VD_1$ and $VD_2$, an optical delay generator ODG', detectors $BD_1$ and $BD_2$ and 3 dB couplers 162, 164, 166, 168, 170 and 172. The variable delay elements $VD_1$ and $VD_2$ are introduced to adjust the coherence gate positions for each channel. The two channels are coupled to samples $S_1$ and $S_2$ which may be two points at different locations in a tissue sample. The light source L' is shared between the two channels in this case, with the optical power in channel 1 being twice that in channel 2. Therefore, channel 1 should be used to scan a deeper region of tissue than channel 2. The 1 to 2 tree coupler TC1 is used so that both channels can share the same reference arm (comprising the phase modulator φMOD' and the optical delay generator ODG'). The ability to share the same reference arm allows one phase modulator to be used to is phase modulate the optical radiation from the multiple single mode fibers 10 (i.e. all the channels). Note that the two channels are combined into one fiber by the tree coupler TC1 and then fed to the same phase modulator φMOD'. Accordingly, cost and complexity of the two channel interferometer 160 is reduced.

Figure 11C:
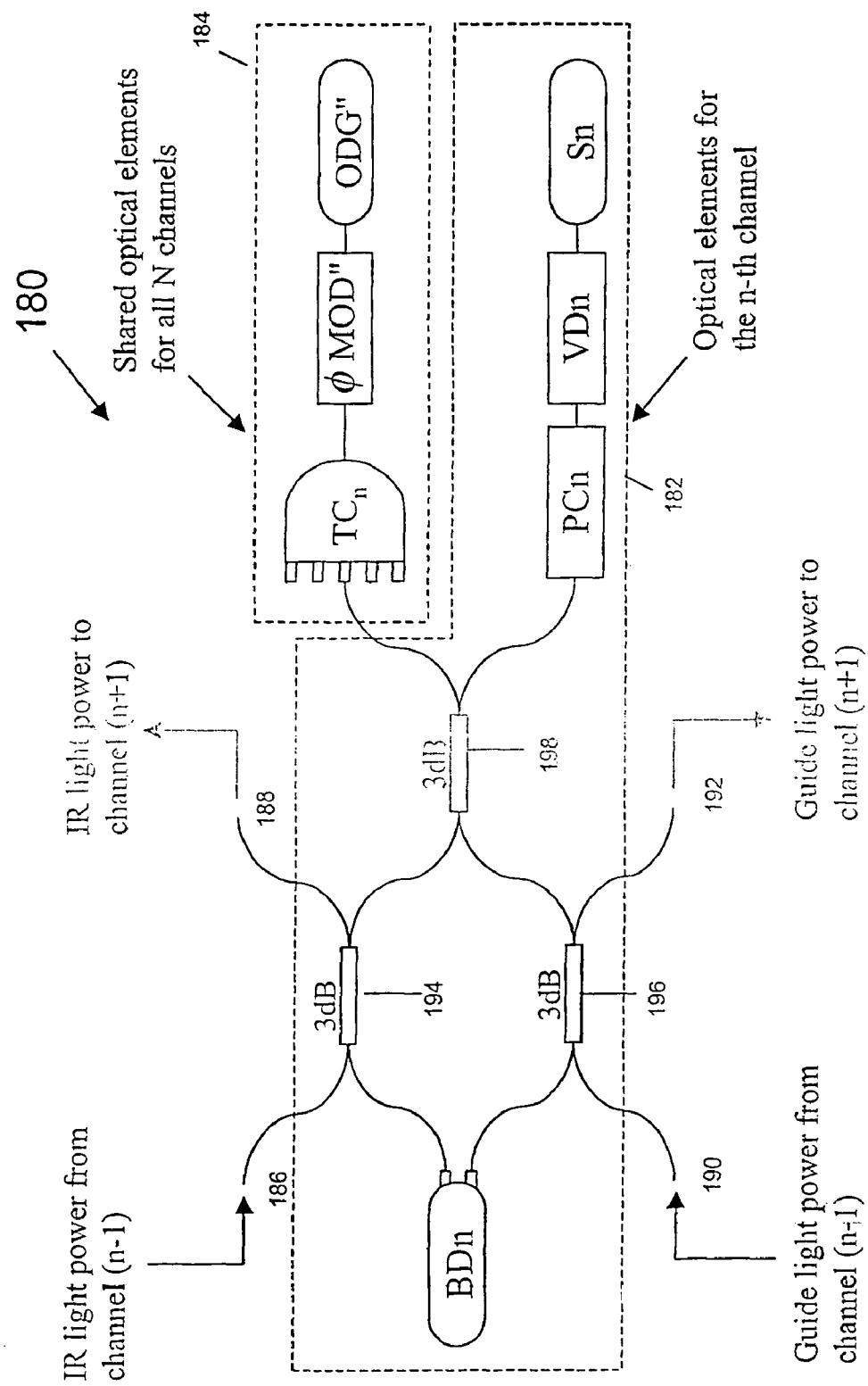
FIG. 11c is a schematic diagram of an optical network that could be used to construct an N-channel Optical Coherence Tomography device.

Based on FIG. 11b, it is conceivable that a general optical network can be used to construct an N channel OCT system such as optical network 180 shown in FIG. 11c. The optical network 180 comprises an optical network for an $n^{th}$ channel 182 and a reference arm 184 that is shared by all n channels. The optical network for the $n^{th}$ channel 182 comprises a detector $BD_n$, 3 dB couplers 194, 196 and 198 and a sample arm comprising a polarization controller $PC_n$ and a variable delay element $VD_n$ connected to a sample $S_n$. The optical network for the $n^{th}$ channel 182 receives optical source radiation 186 from the $n-1^{th}$ channel and transmits optical source radiation 188 to the $n+1^{th}$ channel via 3 dB coupler 194. The optical network for the $n^{th}$ channel 182 receives guide light power 190 from the $n-1^{th}$ channel and sends guide light power 192 to the $n+1^{th}$ channel via 3 dB coupler 196. In this embodiment, a light source (not shown) may be shared between each of the N channels with a power distribution that follows a geometric series or another suitable power partition scheme. The reference arm 184, comprising an N to 1 tree coupler TCn, a phase modulator φMOD" and an optical delay generator ODG", is shared between each of the N channels.

Each of the schematics shown in FIGS. 11a, 11b and 11c, suffer from the fact that a portion of the optical radiation of the interference pattern, from the interference between the reflected optical radiation from the sample and reference arms, which is sent from the 3 dB coupler connected to the detector is lost. In this case 50% of the optical radiation of the interference pattern is lost since a 3 dB coupler is used. For instance in FIG. 11a, only 50% of the optical radiation of the interference pattern is sent from 3 dB couplers 140 and 142 to the detector BD. This makes it more difficult to detect the interference pattern especially for interference patterns with low intensities. To address this, a non-reciprocal optical device, such as an optical circulator may be used to send, to a detector, the portion of the optical radiation that would have been lost if only a 3 dB coupler were used.

Figure 12A:
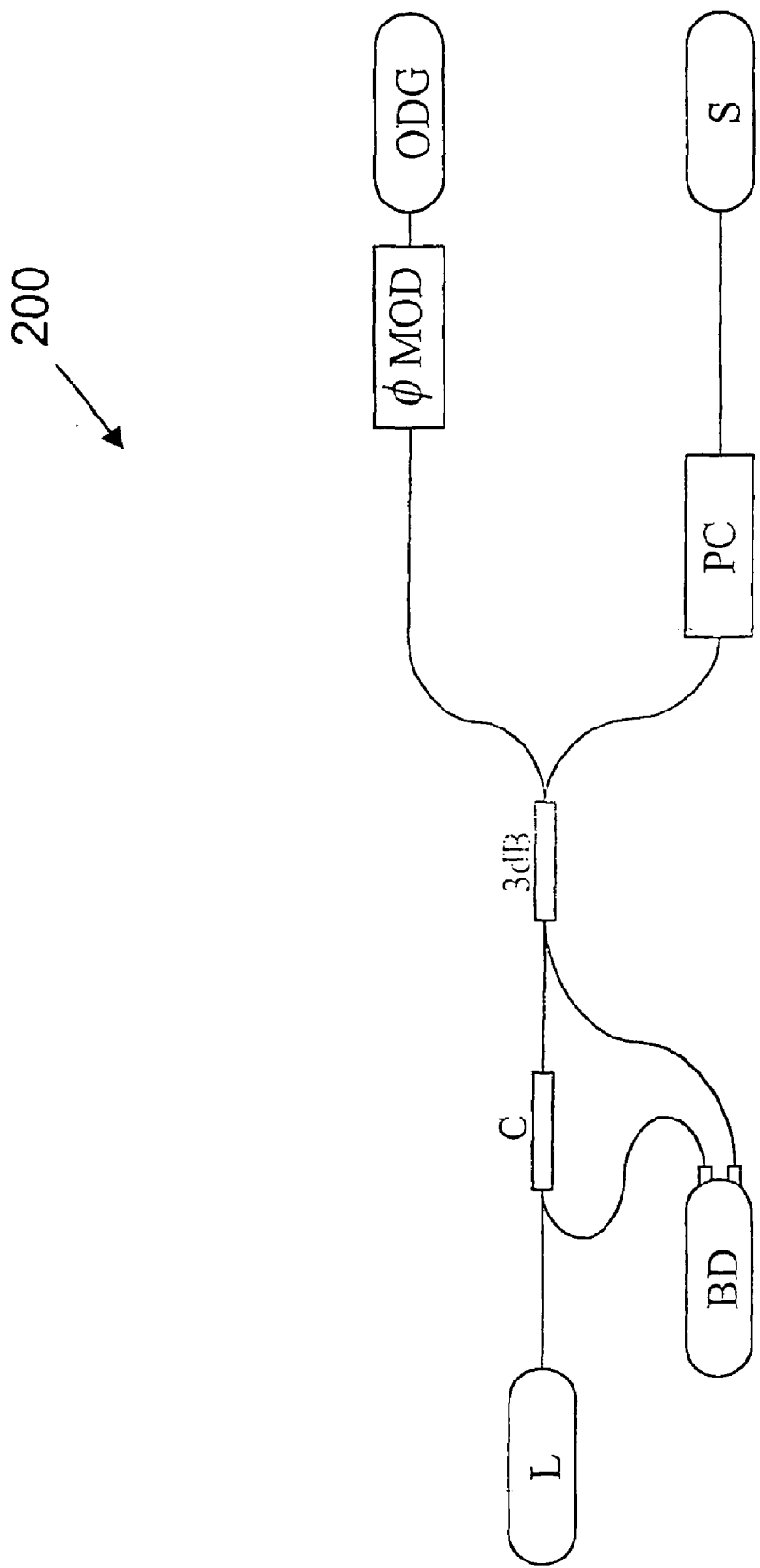
FIG. 12a is a schematic diagram of a single channel Optical Coherence Tomography device with an optical circulator.
Figure 12B:
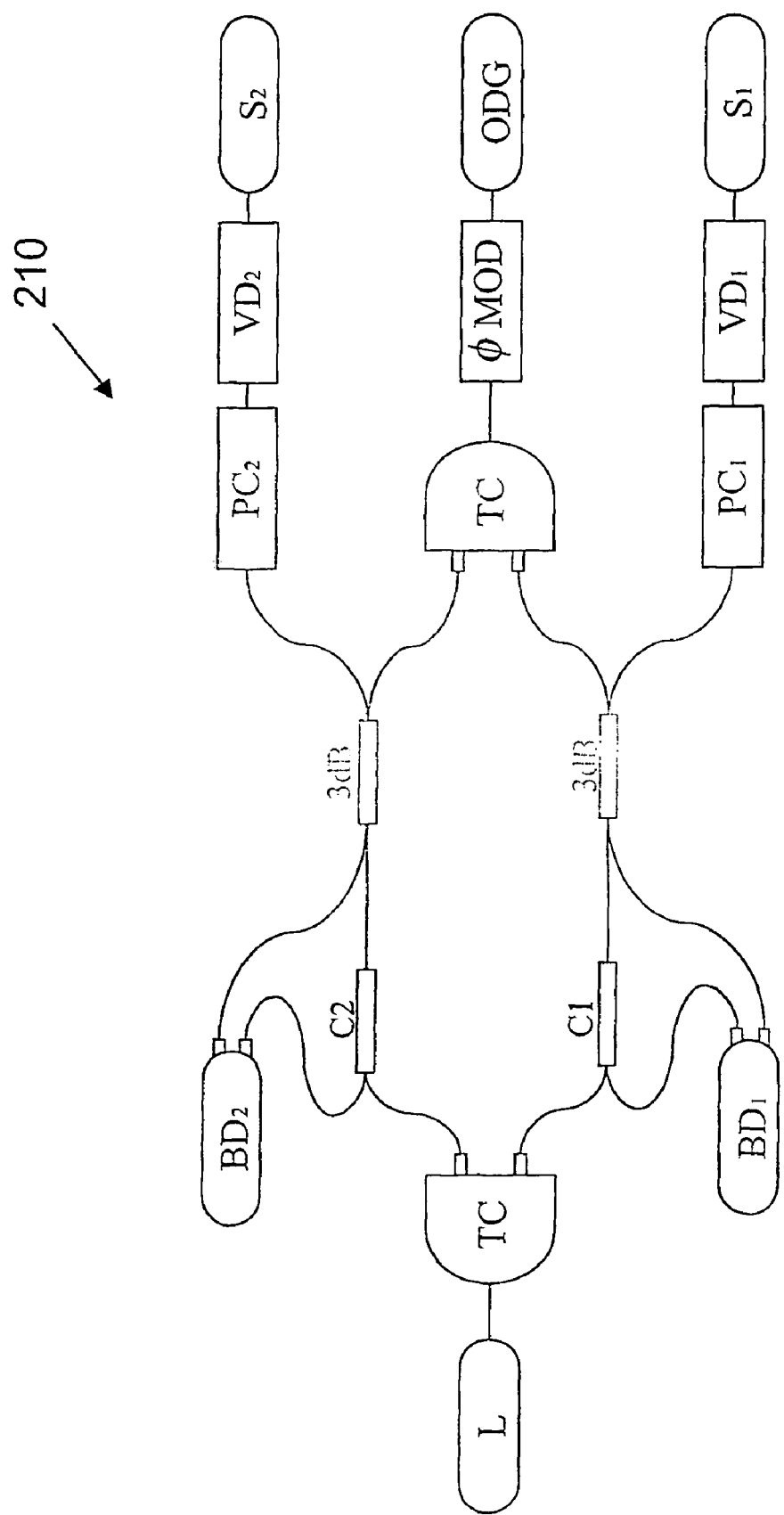
FIG. 12b is a schematic diagram of a two channel Optical Coherence Tomography device employing optical circulators.
Figure 12C:
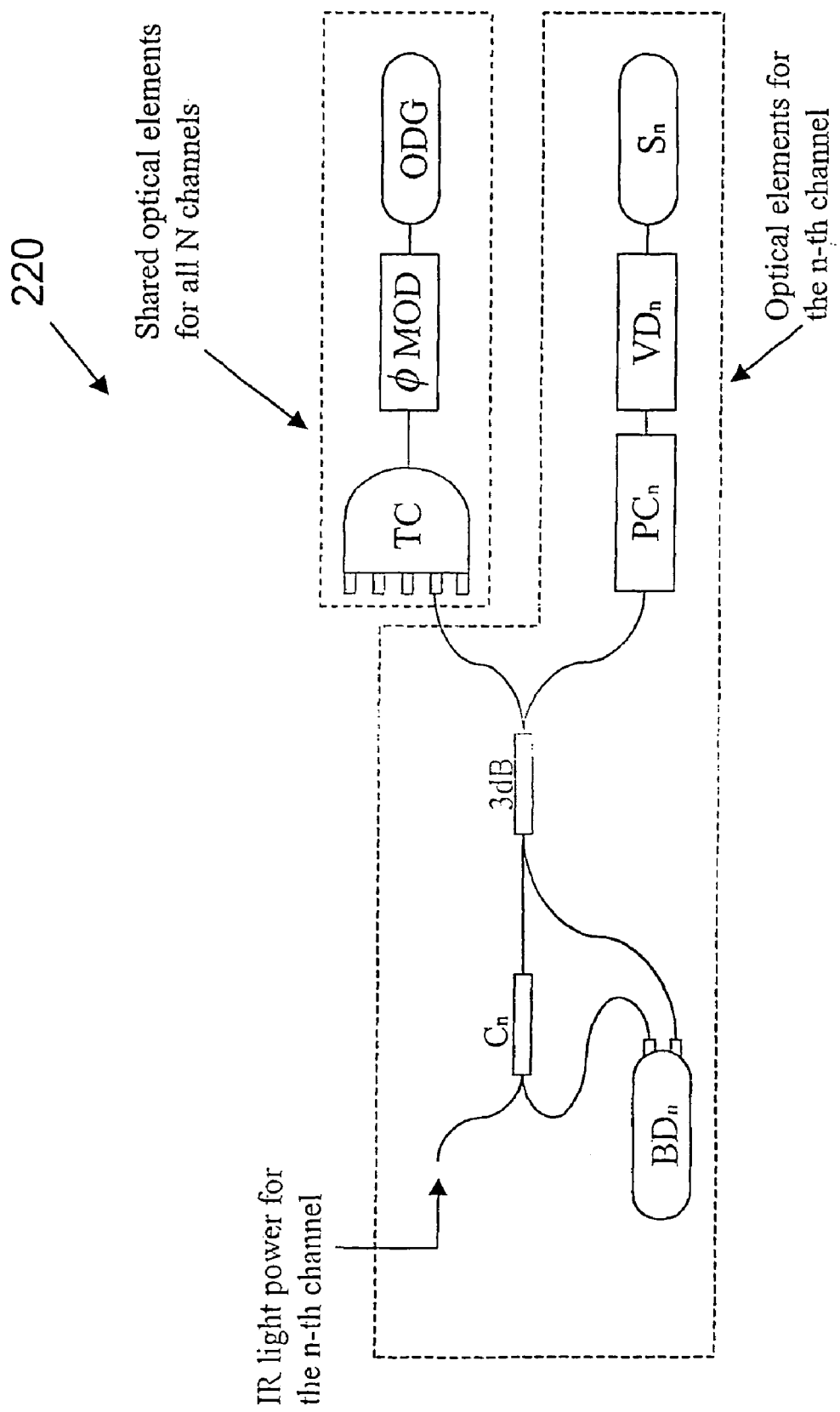
FIG. 12c is a schematic diagram of an optical network that could be used to construct an N channel Optical Coherence Tomography device employing an optical circulator.

Referring to FIGS. 12a, 12b and 12c, alternate embodiments of a single channel OCT device 200, a two channel OCT device 210 and an optical network for an N channel OCT device 220 are shown comprising optical circulators. In FIGS. 12a, 12b and 12c, the optical circulators C, $C_1$, $C_2$ and $C_n$ are used to salvage and direct the optical radiation of the interference pattern to the detectors BD, $BD_1$, $BD_2$ and $BD_n$ respectively to provide a larger intensity interference signal for detection. The rest of the components in these embodiments are similar to those in the of the single channel OCT device 150, the two channel OCT device 160 and the optical network for the N channel OCT device 180 shown in FIGS. 11a to 11c. The concept of using optical circulators to salvage optical radiation and provide the salvaged optical radiation to a detector may also be applied to the apparatus of FIG. 6 in which optical circulators could be placed between the 3 dB couplers and the detectors.

The schematic shown in FIGS. 11c and 12c leads to an elegant design, however, parallel interferometers that share components (i.e. a phase modulator) may produce prohibitive amounts of channel cross talk which may consequently lead to image degradation. However, with fiber length mismatching between channels, cross talk may be effectively handled. Electronic cross-talk can be handled using standard shielding and grounding techniques. The following describes the optical cross-talk.

Figure 13A:
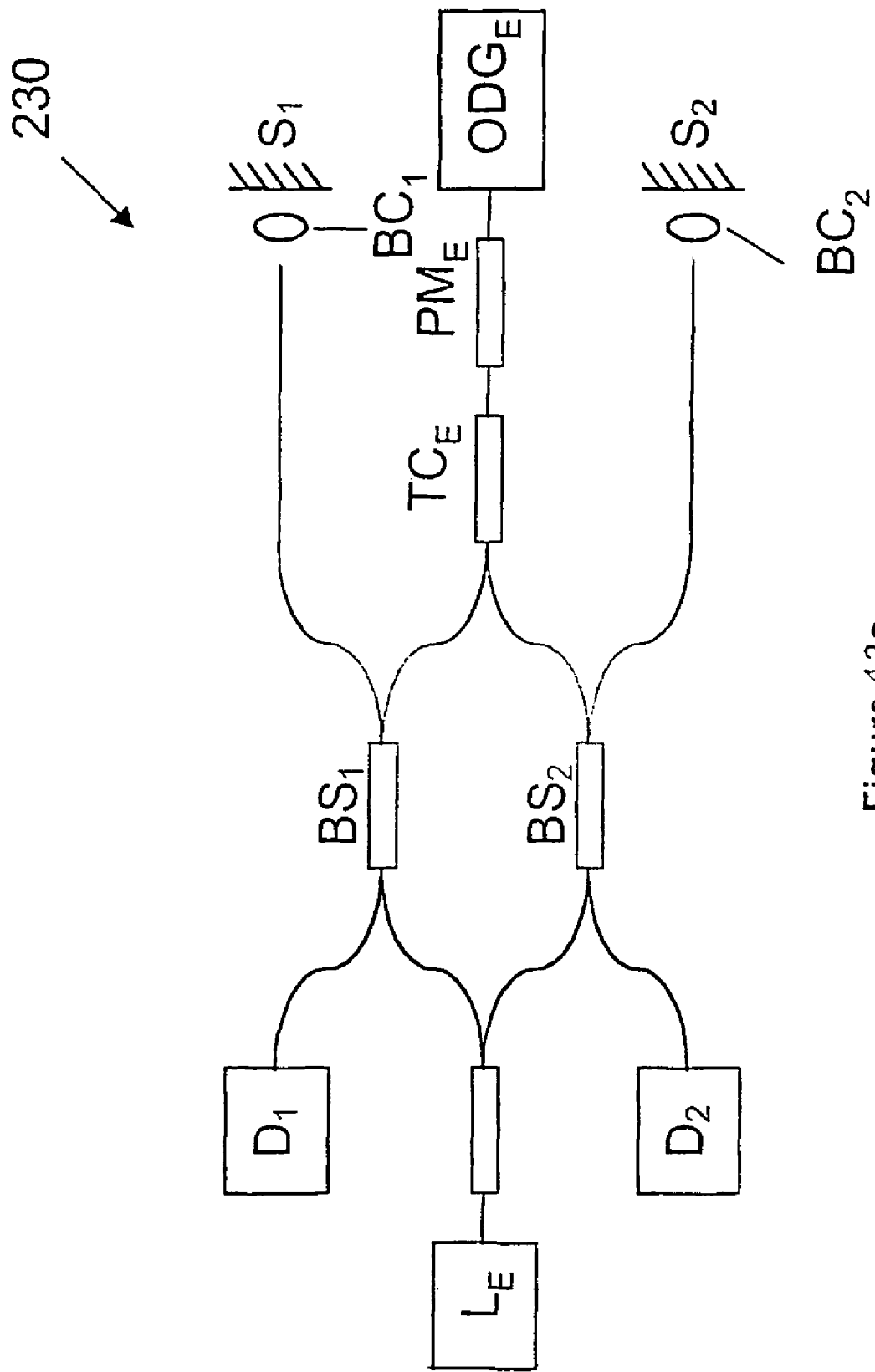
FIG. 13a is a schematic of an experimental setup used to investigate cross-talk between optical channels sharing components.

Referring now to FIG. 13a, a two channel OCT system 230 was assembled to investigate channel cross talk. The two channel OCT system 230 comprises a laser $L_E$, detectors $D_1$ and $D_2$, beam splitters $BS_1$ and $BS_2$, a 1 to 2 tree coupler $TC_E$, a phase modulator $PM_E$, an optical delay generator $ODG_E$, beam collimators $BC_1$ and $BC_2$ and two mirrors $S_1$ and $S_2$ which simulate samples. In the two channel OCT system 230, the desired imaging signals come from the channel 1 and channel 2 optical paths. The desired imaging signal for channel 1 occurs when light from the optical pathway:

$$L_E \to BS_1 \to S_1 \to BS_1 \to D_1 \tag{20}$$

interferes coherently with light from the optical pathway:

$$L_E \to BS_1 \to ODG_E \to BS_1 \to D_1 \tag{21}$$

and is detected by the detector $D_1$. The desired imaging signal for channel 2 occurs when light from the optical pathway:

$$L_E \to BS_2 \to S_2 \to BS_2 \to D_2 \tag{22}$$

interferes coherently with light from the optical pathway:

$$L_E \to BS_2 \to ODG_E \to BS_2 \to D_2 \tag{23}$$

and is detected by the detector $D_2$. Furthermore, OCT imaging in the two channels occurs only when the optical distance $BS_1 \to S_1$ is equal to the optical distance $BS_1 \to ODG_E$ and when the optical distance $BS_2 \to S_2$ is equal to the optical distance $BS_2 \to ODG_E$. Otherwise, image degradation could occur from constructive interference of light reflected from two (or more) different paths that are not the desired imaging paths stated above.

Based on the optical network shown in FIG. 13a, there may be two major classes of potential cross talk. The primary source of cross talk may be coherent light that is reflected (from a mirror or the sample) from one channel's beam splitter into the other channel's beam splitter and detector. Such cross talk would have intensities equal to the imaging signal intensities and could potentially cause significant image degradation. Reflection from one channel to the other could occur at the optical delay generator $ODG_E$ or at the samples $S_1$ or $S_2$. Therefore, light from the optical pathway:

$$L_E \to BS_1 \to S_1 \to BS_1 \to D_1 \quad (20)$$

may interfere with light from the optical pathway:

$$L_E \to BS_2 \to ODG_E \to BS_1 \to D_1 \quad (24)$$

Alternatively, light from the optical pathway:

$$L_E \to BS_2 \to S_2 \to BS_2 \to D_2 \quad (22)$$

may interfere with light from the optical pathway:

$$L_E \to BS_1 \to ODG_E \to BS_2 \to D_2 \quad (25)$$

Sample arms 1 and 2 would not normally be separated as they are in FIG. 13a because the sample arms would be aimed at different points (i.e. different depths) on a tissue sample. When the sample arms are not separate, reflection could occur from, channel 1 into channel 2 and vice-versa. In such a case, light from the optical pathway:

$$L_E \to BS_2 \to S_2 \to BS_1 \to D_1 \quad (26)$$

may interfere with light from the optical pathway:

$$L_E \to BS_1 \to ODG_E \to BS_1 \to D_1 \quad (21)$$

Alternatively, light from the optical pathway:

$$L_E \to BS_1 \to S_1 \to BS_2 \to D_2 \quad (27)$$

may interfere with light from the optical pathway:

$$L_E \to BS_2 \to ODG_E \to BS_2 \to D_2 \quad (23)$$

It should be recalled that reflection may also occur at undesirable locations such as beam splitters and connector insertion points. Conceivably, such reflections may contribute to image noise if the light from these pathways produced interference fringes having a significant intensity. However, this kind of noise may be secondary to the channel cross talk previously described because of its lower intensity.

Analysis of the system revealed that the worst-case scenario for interference of such back-reflections involves one reflection from a connector. For example, light from the following optical path:

$$L_E \to BS_1 \to S_1 \to BS_1 \to D_1 \quad (20)$$

may interfere with light from the optical pathway:

$$L_E \to BS_2 \to ODG_E \to PM_E \to ODG_E \to BS_1 \to D_1 \quad (28)$$

There are four possible outcomes for the interference of light from any two pathways and the outcome depends on path length difference. Firstly, if the path lengths are identical, then the intensity of the interference fringes at the detector will be greater than the true signal intensity based solely on the sample reflectivity. This sort of image noise would not be detectable as noise and would alter the measured sample intensity throughout the image. Fortunately, the probability of the path lengths matching exactly is remote. A second possibility is that the path lengths could match to within the coherence length of the light source. This situation would result in an increase in the width of the interference fringe envelope and consequently degradation in axial resolution. Thus situation is unlikely, but it may be detected by measuring the full-width-half-maximum of the mirror surface depth profile. A third possibility involves the path lengths differing by a distance greater than the coherence length of the source $L_E$ and less than the scanning depth of the optical delay generator $ODG_E$. This situation may manifest as two separate coherence envelopes within one depth sweep by the optical delay generator $ODG_E$. The final and most likely possibility is that the path lengths differ by more than the scanning depth of the optical delay generator $ODG_E$ and no noise or extraneous interference fringes will be detected by the system.

The primary type of channel cross talk should be unlikely because of fiber optic manufacturing. Optical path lengths $BS_1 \to ODG_E$ and $BS_2 \to ODG_E$ are essentially predetermined by the lengths of the fiber pigtails coming from beam splitters $BS_1$ and $BS_2$. Optical path lengths $BS_1 \to S_1$ and $BS_2 \to S_2$ are deliberately matched to the predetermined corresponding reference arm lengths. Typically manufactured fiber lengths differed by several tens of millimeters which is at least one order of magnitude greater than the scanning depth of the optical delay generator $ODG_E$. Therefore, this type of cross talk should not be a problem in a dual channel system.

In the case of insertion point reflections, if the optical distance $PM_E \to ODG_E$ matched the path length difference between optical paths $BS_1 \to S_1$ and $BS_2 \to ODG_E$, then interference fringes and image degradation may occur. Again, this sort of secondary noise should be unlikely because the fiber lengths are about 300 mm while the optical delay generator $ODG_E$ scans through only a couple of millimeters. Furthermore, the intensity of such interference fringes would be lost in the system noise. Secondly, the equipment used has a maximum 0.6 dB insertion loss (in other words a maximum of reflection of 0.6 dB) and therefore such a signal is below the detection limits used in the setup of FIG. 13a.

To demonstrate that two channels can use the same fiber and optical components, the OCT system 230 was evaluated. The sample arm mirrors $S_1$ and $S_2$ were placed such that the sample arm optical path length and the optical delay generator $ODG_E$ reference arm optical path length matched for each channel and a set of interference fringes were seen at each of the detectors $D_1$ and $D_2$. The sample arms for samples $S_1$ and $S_2$ were kept separate for alignment purposes and to eliminate the possibility of light from channel 1 reflecting into the fiber containing channel 2 and vice-versa. Although an optical delay generator could be used to produce both phase modulation and group delay (Tearney et al. 1997), with the setup shown in FIG. 13a, the optical delay generator $ODG_E$ was used for group delay (i.e. depth scanning) while the phase modulator $PM_E$ in the reference arm was used to produce phase delay.

In the experimental setup of FIG. 13a, the light source $L_E$ comprised a 1310 nm, 9 mW light source (model BBS1310) made by AFC Technologies Inc. The central wavelength of the light source $L_E$ was 1310 nm with a measured spectral spread of ±40 nm. The measured coherence length of the light source $L_E$ was 10 μm. The detectors $D_1$ and $D_2$ were 155 Mbps Perkin Elmer InGaAs photodiode receivers with a detection band centered at 1310 mm having a bandwidth greater than or equal to 100 nm. The phase modulator $PM_E$ was a JDS Uniphase 43 MHz phase modulator. The beam splitters $BS_1$ and $BS_2$ were made by MetroTek. OZ Optics manufactured the beam collimators $BC_1$ and $BC_2$. Alternate suitable components may be used from these or other suppliers.

The optical delay generator $ODG_E$ dispersed the collimated light using a 150 line/mm diffraction grating blazed for 1310 nm which was made by CVI Spectral Products. A Melles Griot glass doublet lens with a 30 mm diameter and 100 mm focal length was used to focus light onto the oscillating mirror. EOPC (Electro-Optical Products Corporation) manufactured the resonant scanner that operated at 8 kHz and scanned through a ±1° mechanical or a ±2° optical angle. This angular setting corresponded to a depth scan of about 1 mm in the sample arms for the samples $S_1$ and $S_2$. Scanning depth is an important consideration in terms of mismatching the optical lengths of the two channels. For instance, if the optical path lengths differ by more than 1 mm then cross talk between the two channels should be minimal and proper shielding and grounding techniques should address electronic cross-talk as well.

Figure 13C:
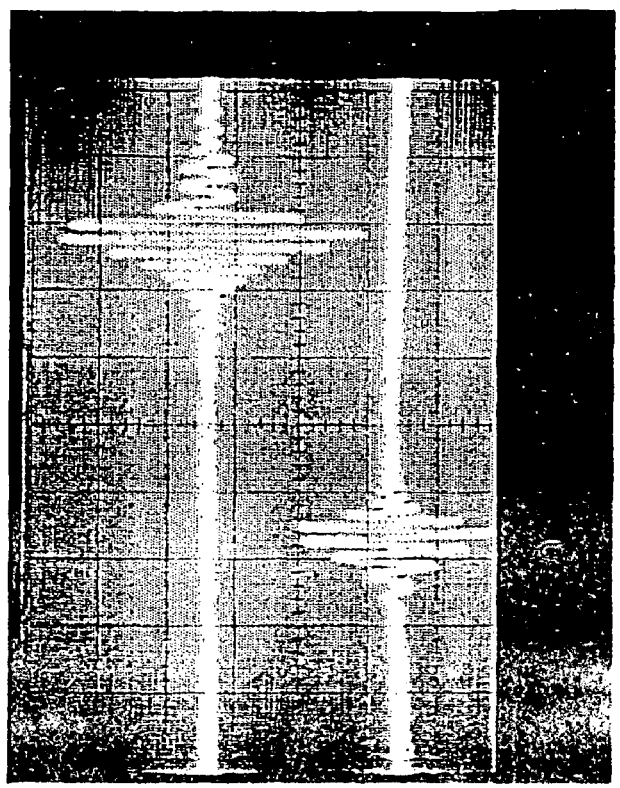
Figure 13B:
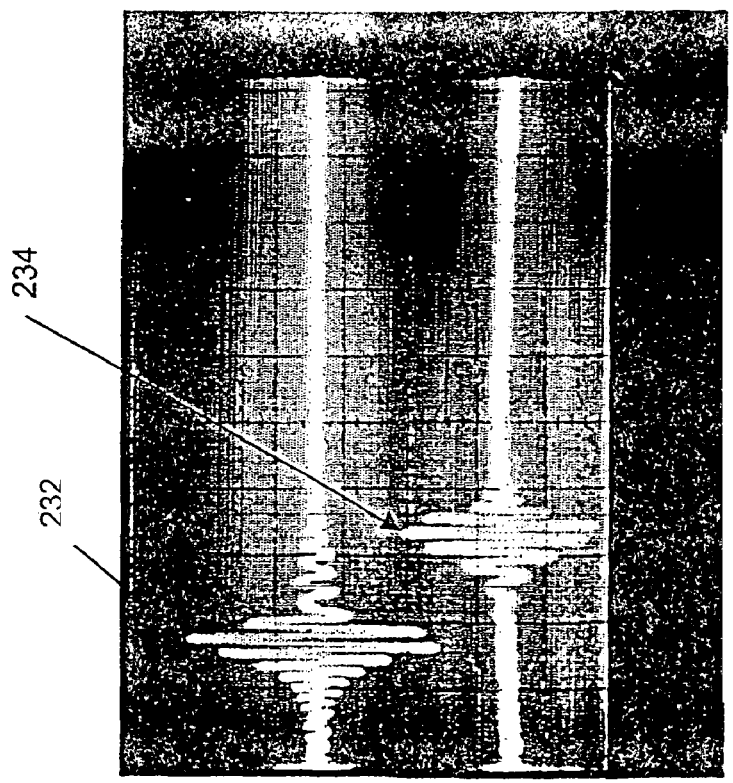

FIGS. 13b and 13c show results from experiments conducted on the setup shown in FIG. 13a. FIG. 13b shows the oscilloscope trace from the detectors $D_1$ and $D_2$ in channel 1 and channel 2. FIG. 13b shows that the interference fringes occur at different points in the cycle of the optical delay generator $ODG_E$ which reflects the slightly different positioning of the two channels within the cycle of the optical delay generator $ODG_E$, i.e. the sample arm mirrors $S_1$ and $S_2$ were deliberately offset by a small amount to simulate imaging at different depths. FIG. 13b shows that there is a strong imaging signal in each of the channels and no evidence of any cross talk. The arrows 232 and 234 indicate reflection from two different sample points which could correspond to two different points in a tissue sample. Furthermore, the full-width-half-maximum of the envelope of each detected pulse corresponded to the coherence length of the light source $L_E$ which indicates that the light signal in each channel originated from the light source $L_E$. FIG. 13c shows the experimental results when one of the sample points was moved relative to the other sample point. In this case, cross-talk was also not observed.

Figure 14:
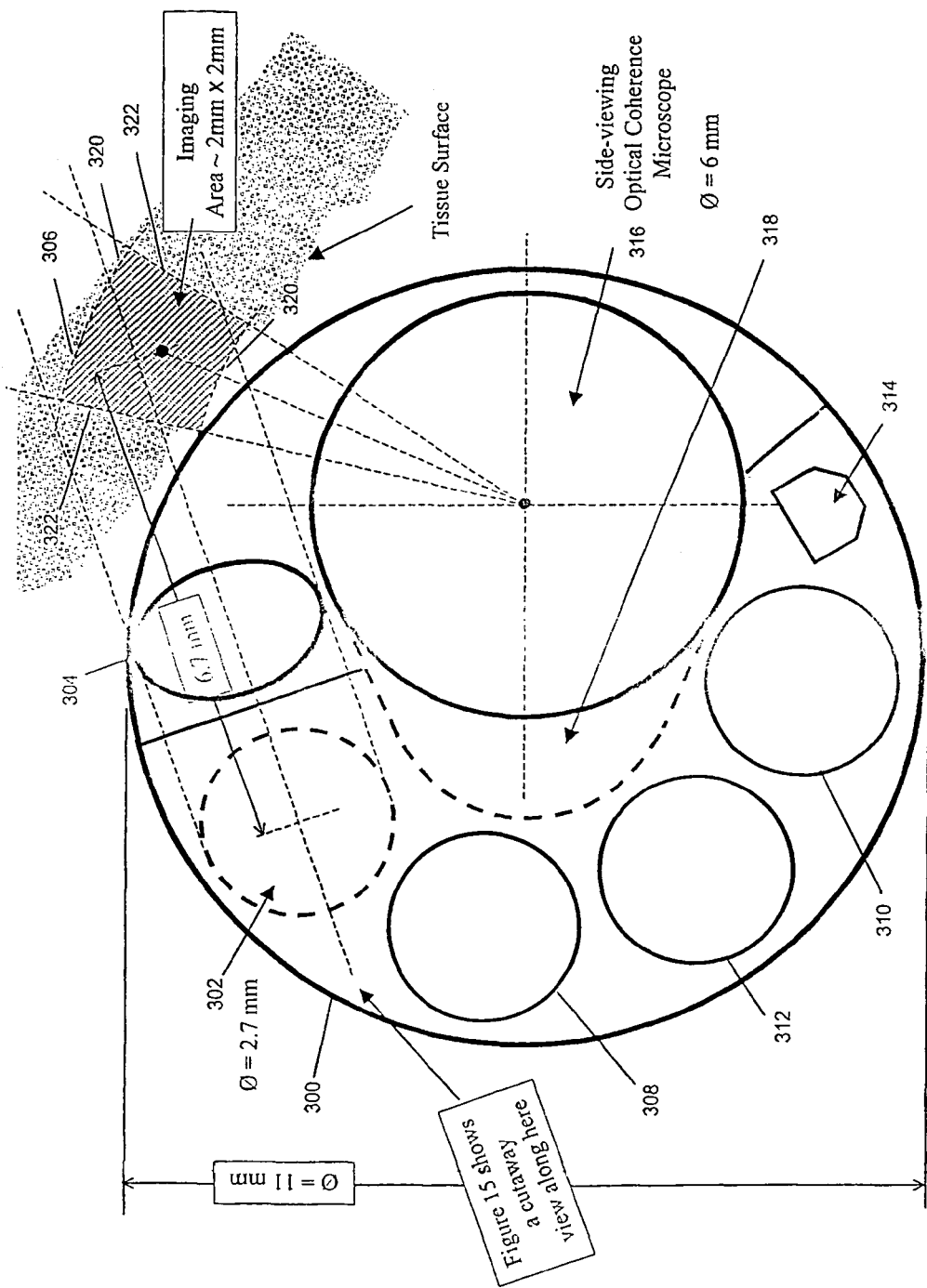
FIG. 14 is an end view of a GI endoscopic coherent optical microscope in accordance with the present invention.
Figure 16:
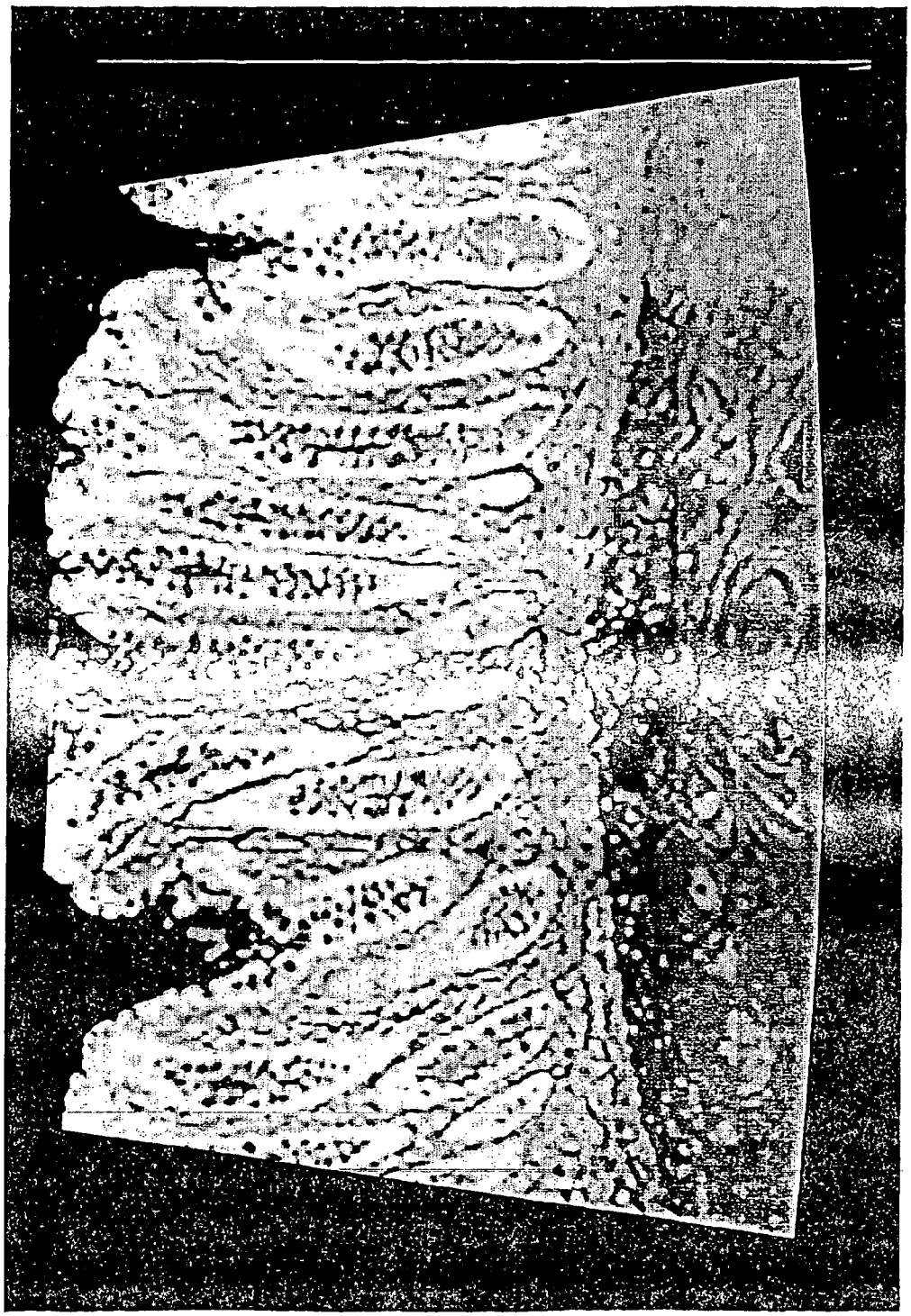
FIG. 16 is a simulated image of a human colon epithelium that is expected to be obtained with the apparatus of the present invention.

In another embodiment of the invention, the fiber optic network, previously disclosed herein, is incorporated into an endoscope so that the multi-channel OCT methodology may be used clinically. Due to the size of the fiber bundle tip 12 of the apparatus, the fiber bundle tip 12 will not fit into the working channel of a conventional diagnostic endoscope (although it may be incorporated into the larger-diameter therapeutic endoscopes). Therefore, an alternate design approach was taken. Instead of designing the fiber bundle tip 12 to accommodate the working channel of a conventional diagnostic endoscope, all of the functionality of a conventional diagnostic endoscope was designed around the fiber bundle tip 12. As shown in FIG. 14, one embodiment of a GI endoscope 300 (corresponding to the tip 56 of FIG. 6) incorporating the endomicroscope of the present invention is approximately 11 mm in diameter. This is slightly larger than the conventional diagnostic endoscope which is 8–9 mm in diameter. The GI endoscope 300 has the endomicroscopy capability disclosed above in addition to conventional forward-viewing white light imaging. Therefore, a user of the GI endoscope 300 should be able to obtain a 2 by 2 mm cross-sectional image as illustrated in FIG. 16.

The GI endoscope 300 includes a 2.7 mm diameter suction/biopsy channel 302. The end of the suction/biopsy channel 302 is bent so as to present an opening 304 directed towards the tissue area of interest 306. The axis of the suction/biopsy channel 302 may be on the order of 6.7 mm from the center of the tissue area of interest 306. Two channels 308 and 310 are provided for white light illumination and a channel 312 is provided for white light endoscope forward viewing. Each of the channels 308, 310 and 312 may have a diameter of 2.7 mm. A small channel 314 is also provided for an air or water nozzle.

In accordance with the present invention, a side-viewing Endoscopic Coherent Optical Microscope (ECOM) 316 is provided in the GI endoscope 300. The side-viewing ECOM 316 includes a drive mechanism 318 for rotating the mirror 16 (not shown in FIGS. 14 and 15). As mentioned previously, radial, translational or helical scanning may be employed. Furthermore, as previously mentioned, a MEMS drive mechanism may be used instead of a mechanical drive mechanism. The side-viewing ECOM 316 is configured to scan through the tissue area of interest 306 having the depth set by the boundaries 320 and the angular extent set by the boundaries 322. Additionally an optical window 324 may be provided for the side-viewing ECOM 316 (see FIG. 15).

Figures 17A, 17B:
FIG. 17a has two panels which each show a microscopy image of sweat ducts in the human skin; and, FIG. 17b has three panels which each show an in vivo OCT image of sweat ducts in the human skin.

The forward-viewing white light channel 312 is updated at a rate of 30 frames/sec. The cross-sectional images obtained by the side-viewing ECOM 316 are updated at 4.4 frames/sec. All imaging channels are displayed simultaneously. The images that may be generated by the GI endoscope 300 are illustrated in FIGS. 16 and 17. FIG. 16 shows a simulated image of a human colon epithelium incorporating the expected spatial resolution which may achievable with the side-viewing ECOM 316. FIGS. 17a and 17b are a comparison of microscopy imaging versus in vivo OCT imaging. FIG. 17a has two panels which each show a microscopy image of sweat ducts in the human skin. FIG. 17b has three panels which each show an in vivo OCT image of sweat ducts in the human skin. The in vivo OCT images were generated with a light source operating at a wavelength of 1300 nm.

Figure 15:
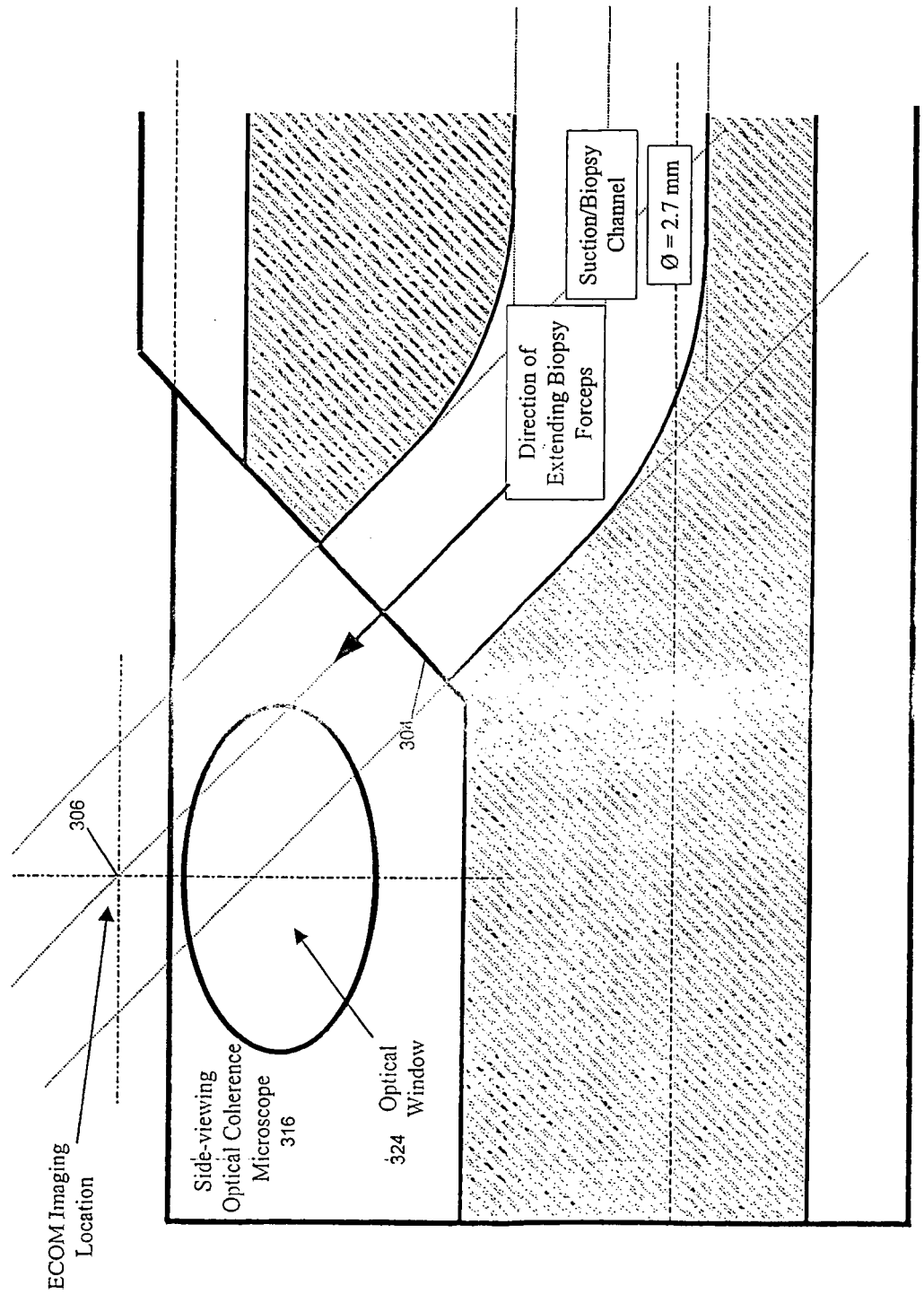
FIG. 15 is a cutaway side view of the GI endoscopic coherent optical microscope of FIG. 14 showing a biopsy channel.

Typical maneuvers or use of the GI endoscope 300 by an endoscopist will incorporate the following steps:

a) Following the steps of a general endoscopy procedure, the GI endoscope 300 is inserted under the guidance of the conventional forward-viewing white light channel 312. This maneuver should be no different from that of currently available GI endoscopes.

b) When the endoscopist needs to make microscopic examinations, he/she first pushes the GI endoscope 300 into contact with the wall of the lumen as shown in FIG. 13. The optics are designed such that when the GI endoscope 300 is in contact with the tissue, the correct working distance of the entire optical system is obtained. Although the GI endoscope 300 is in contact with the wall, the part of the tissue under microscopic examination is not, as illustrated in FIG. 15. Therefore, the surface features of the tissue are not distorted by contact pressure. However, this does not imply that the GI endoscope 300 can only be operated in a contact mode. In fact, the GI endoscope 300 may be operated in a non-contact mode, as long as images are formed, which is dictated by whether the previously described dynamic triggering algorithm has found an air-tissue interface. If the air-tissue interface lies within the working distance of the system then the interface should be specific and easily detected since the interface produces clear peaks in the detected light pattern as previously described in the 'flexible triggering' method.

c) If the endoscopist needs to examine a region adjacent to the area imaged in step (b), then the endoscopist can torque the GI endoscope 300 and rotate the field of view to a new location.

The best techniques currently in use for visualization of the gastrointestinal (GI) tract include endoscopic ultrasonography (EUS) and magnification endoscopy (ME). The resolution of high-frequency EUS, approximately 70 to 100 mm, is insufficient for the identification of many conditions that perturb tissue microstructure, most notably subtle pathologic changes arising within the superficial layers of the GI tract (mucosa and submucosa). ME, with a magnification of up to 170×, provides excellent images of fine superficial mucosal patterns but subsurface structures and lesion staging cannot be determined. Accordingly, tissue biopsy and histology currently remain the standard of care for detecting microscopic diseases involving the GI tract.

The side-viewing ECOM 316 disclosed herein may achieve real-time, 2 mm deep cross-sectional images of the GI wall at a resolution of 5 µm in both axial and transverse (lateral) dimensions. For reference, gastrointestinal epithelial cells average 7 to 10 µm in size which increases further as dysplastic or neoplastic transformation ensues. In the GI tract, a depth of view at 2 mm is nevertheless sufficient to detect mucosally-based diseases as well as any neoplastic invasion into the underlying submucosa, which is of important for prognostic and therapeutic purposes. The image resolution of the side-viewing ECOM 316 may correspond to observing an unstained histology slide under a 100× (total magnification) microscope. Accordingly, many important entities such as dysplasia (cellular neoplastic alterations) or neoplastic violation of structures such as the lamina propria or muscularis mucosae may be discernible with the side-viewing ECOM 316.

The present invention may allow for in-situ diagnosis of diverse microscopic mucosal pathologies and lesion staging. In essence, this "optical biopsy" technique may replace, or at the very least, guide the standard biopsy and histology method. This may translate into reducing unnecessary biopsy samples and tissue processing, decreasing patient risk and increasing sampling rate and diagnostic yield thus providing immediate diagnostic feedback both to the physician and the patient and targeting biopsies (which in itself may become a therapeutic maneuver in some cases). Pre-neoplastic GI conditions such as Barrett's esophagus, chronic ulcerative colitis, early flat adenomas, or foci of aberrant colonic crypts, to name a few, may be applicable to the side-viewing ECOM 316. Currently, detection and surveillance of neoplastic progression within these conditions are suboptimal due to their microscopic nature.

Secondly, the side-viewing ECOM 316 may serve as a functional imaging system permitting monitoring of neoplastic and non-neoplastic tissue alterations over time. For instance, the recovery of the structure of small intestinal villi and reduction in inflammatory cells may be monitored by the side-viewing ECOM 316 in diverse malabsorptive disorders of the gut such as gluten-sensitive enteropathy, tropical sprue and intestinal infestation. The natural history of many mucosal diseases at the microscopic level may also be assessed in a minimally invasive manner. The ability to monitor structural cellular changes that are occurring in vivo with time may provide important physiologic information on cellular function and insight into cellular pathologic transformation.

Thirdly, the side-viewing ECOM 316 may be used in the monitoring of tissue post therapy. In vivo microscopic evaluation of surgical resection margins or treatment margins during post-therapeutic surveillance of cancer resection or assessment of the adequacy of photodynamic therapy of mucosal preneoplastic conditions are only some examples.

Applications in other medical specialties may also be possible. It should be understood by those skilled in this art that the multichannel OCT apparatus disclosed herein may have application in a large number of medical specialties such as dermatology, hematology, oncology (medical and radiation), ophthalmology, urology, surgery, respirology and gastroenterology.

The multichannel OCT system disclosed herein may be altered to further improve system performance. For instance a modification that may be made would be to employ coded transmission for the optical radiation which is radiated from the optical sources. This technique may increase the image resolution by increasing the SNR of the optical radiation of the interference pattern obtained in channels which suffer from poor SNR.

It should be understood that various modifications can be made to the preferred embodiments described and illustrated herein, without departing from the present invention, the scope of which is defined in the appended claims. For instance, in each of the schematics, herein disclosed, other optical couplers may also be used in place of the 3 dB couplers.

The invention claimed is:

1. An apparatus for optical examination of a sample, the apparatus comprising:
    an optical source means for providing a plurality of separate optical radiation sources;
    a first optical path extending from the optical source means;
    a focusing means in the first optical path for focusing optical radiation from the optical radiation sources into a plurality of respective focal points located on a surface within the first optical path to provide substantially continuous coverage of a selected portion of the first optical path, wherein, in use, a sample can be located at least partially within said selected portion, thereby permitting simultaneous scanning of a plurality of points within the sample,
    wherein the optical source means comprises optical coupling means having one of a plurality of optical fibers and a plurality of optical waveguide wafers, wherein ends of the plurality of optical fibers or the plurality of optical waveguide wafers are stepped relative to one another along the first optical path and wherein optical radiation from each optical fiber or each optical waveguide wafer is focused to a different focal point on the surface of the first optical path.

2. An apparatus as claimed in claim 1, wherein the optical source means further comprises a primary optical source and wherein the optical coupling means connects the primary optical source to the optical radiation sources.

3. An apparatus as claimed in claim 2, which further includes a plurality of optical couplers between the primary optical source and the optical fibers, an optical delay generator coupled to the optical couplers and detector means coupled to the optical couplers, wherein the optical couplers transmit a portion of the radiation from the primary optical source along the first optical path and a portion of the radiation from the primary optical source to the optical delay generator, the optical delay generator providing a second optical path, wherein an interference effect occurs between radiation returned along the first and second optical paths to the optical couplers and the optical couplers transmit the radiation returned along the first and second optical paths to the detector means.

4. An apparatus as claimed in claim 3, which includes a plurality of primary optical sources and a plurality of tree couplers, each tree coupler being associated with one primary optical source and coupling said one primary optical source to at least one of the optical couplers.

5. An apparatus as claimed in claim 4, which includes a plurality of optical circulators, placed between the optical couplers and the detectors for providing salvaged optical radiation to the detectors.

6. An apparatus as claimed in claim 3, wherein a plurality of optical fibers couple the optical couplers to the optical delay generator, the optical delay generator having a grating and a scanning mirror, the scanning mirror having an axis, wherein the grating separates optical radiation from each optical fiber into spectral components linearly oriented on the scanning mirror, wherein the midpoint of said spectral components is offset from the axis of the scanning mirror by a distance $x_d$ to phase modulate said spectral components.

7. An apparatus as claimed in claim 3, which includes a first plurality of optical fibers for coupling each optical coupler to a phase modulator and a second plurality of optical fibers for coupling each phase modulator to the optical delay generator, the optical delay generator having a grating and a scanning mirror, the scanning mirror having an axis, wherein for each optical fiber, the phase modulator phase modulates the optical radiation and said grating separates said phase modulated optical radiation into spectral components which are linearly oriented on said scanning mirror, the midpoint of said spectral components being centered on the axis of said scanning mirror and wherein the spectral components from each optical fiber is spaced apart from the spectral components of the optical radiation from the other optical fibers.

8. An apparatus as claimed in claim 3, which includes a plurality of optical fibers coupling each optical coupler to a tree coupler for combining optical radiation from each of the optical fibers into a first optical fiber, said first optical fiber connected to a phase modulator for phase modulating said combined optical radiation and including a second optical fiber for coupling said phase modulator and said optical delay generator.

9. An apparatus as claimed in claim 1, wherein the optical source means further comprises a plurality of optical sources (50), and wherein the optical coupling means connects the plurality of optical sources (50) to the optical radiation sources and further includes a plurality of optical couplers (54) adapted to adjust the intensity of the optical radiation provided by each of the plurality of optical fibers (10) or each of the plurality of optical waveguide wafers for facilitating deep or shallow scanning.

10. An apparatus as claimed in claim 1, which includes a rotatable mirror in the first optical path, for deflecting radiation from the optical radiation sources to permit rotational movement of the surface.

11. An apparatus as claimed in claim 10, including a micromachined electro-mechanical system coupled to the mirror for rotating the mirror.

12. An apparatus as claimed in claim 10, wherein the apparatus is configured as an endoscope for internal examination of a body, wherein the first optical path, the focusing means and the mirror are provided in the endoscope, and wherein the endoscope includes at least one of: at least one channel for white light illumination; a channel for white light endoscope forward viewing; a channel for one of an air nozzle and a water nozzle; and a suction/biopsy channel.

13. An apparatus as claimed in claim 12, wherein the endoscope is adapted to perform radial, translational or helical scanning.

14. An apparatus as claimed in claim 13, wherein the endoscope further includes a micromachined electro-mechanical system as a drive mechanism.

15. An apparatus as claimed in claim 1, which includes a mirror in the first optical path and wherein the optical source means, the focusing means and the mirror, in combination, may be linearly translated to permit linear movement of the surface.

16. An apparatus as claimed in claim 15, including a micromachined electro-mechanical system for linearly translating the optical source means, the focusing means and the mirror.

17. An apparatus as claimed in claim 1, which includes a rotatable mirror in the first optical path and wherein the optical source means, the focusing means and the rotatable mirror, in combination, may be linearly translated to permit helical movement of the surface.

18. A method for optical examination of a sample, the method comprising:
  (a) providing radiation from a plurality of separate optical radiation sources, along a first optical path;
  (b) providing focusing means in the first optical path;
  (c) focusing the optical radiation from the optical sources into a plurality of respective focal points along a surface within the first optical path to provide substantially continuous coverage of a selected portion of the first optical path;
  (d) providing a sample located at least partially within the first optical path;
  (e) simultaneously scanning a plurality of points within the sample, and
  (f) providing an optical coupling means for the plurality of separate optical radiation sources wherein the optical coupling means have one of a plurality of optical fibers or a plurality of optical waveguide wafers, wherein the method further comprises stepping the ends of the plurality of optical fibers or the plurality of optical waveguide wafers relative to one another in a common plane along the first optical path for focusing optical radiation from each optical fiber or each optical waveguide wafer through a common lens to a different focal point on the surface of the first optical path.

19. A method as claimed in claim 18, which includes providing radiation from a primary optical source and transmitting the radiation along the plurality of optical fibers or the plurality of optical waveguide wafers to the plurality of separate optical radiation sources.

20. A method as claimed in claim 18, wherein the method further includes providing a plurality of optical sources, connecting the plurality of optical sources to the optical radiation sources and using a plurality of optical couplers to adjust the intensity of the optical radiation provided by each of the plurality of optical fibers or each of the plurality of optical waveguide wafers for facilitating deep or shallow scanning.

21. A method as claimed in claim 18, which includes:
  (a) providing a rotatable mirror in the first optical path;
  (b) deflecting the first optical path;
  (c) causing the plurality of focal points to be located on a surface;
  (d) performing an axial scan;
  (e) performing one of: rotating the mirror to move the surface; linearly translating, in combination, the focusing means, the plurality of optical radiation sources and the mirror to move the surface; and, simultaneously rotating the mirror and linearly translating, in combination, the focusing means, the plurality of optical radiation sources and the mirror to move the surface; and, (f) repeating step (d) at least two times and performing step (e) between each repetition.

22. A method as claimed in claim 21, which includes supplying radiation from the primary optical source through a plurality of couplers to the optical fibers, providing an optical delay generator connected to the optical couplers and providing a second optical path, permitting radiation to be transmitted back along the first and second optical paths to the couplers, for forming interference, and transmitting radiation received from the first and second optical paths at the optical couplers to detection means for detection of the interference pattern.

23. A method as claimed in claim 22, which includes providing a plurality of primary optical sources and, for each primary optical source, a respective tree coupler, and coupling each primary optical source through said respective tree coupler to each of the optical couplers.

24. A method as claimed in claim 23, which includes providing the apparatus as an endoscope adapted for examining an internal cavity of the body, including at least one of: at least one channel for white light illumination, a white light endoscope forward viewing channel, a suction/biopsy channel and a channel for one of an air nozzle and a water nozzle.

25. A method as claimed in claim 22, which includes providing optical circulator means between the optical couplers and the detection means for providing salvaged optical radiation to the detection means.

26. A method as claimed in claim 18, wherein there is a change in refractive index between a medium containing the optical radiation sources and the sample, wherein for each focal point, a distance mismatch due to the change in refractive index between the coherence gate of each optical radiation source and the focal point in the sample is obtained according to the steps of:

(a) scanning optical radiation from the plurality of optical radiation sources in said first optical path such that the focal points of the optical radiation sources are aligned along a path extending from the medium containing the optical radiation sources into the sample;

(b) detecting the reflected optical radiation for each focal point; and, (c) locating the focal point for which there is a large change in reflected optical radiation compared to neighboring focal points, wherein, the focal point located in step (c) indicates the location of the interface between the sample and the medium containing the optical radiation sources.

27. A method as claimed in claim 26, wherein the method further comprises repeating steps (a) to (c) for each axial scan to obtain proper spatial resolution for the selected scan zone.

* * * * *